United States Patent
Prince et al.

(10) Patent No.: US 12,020,440 B2
(45) Date of Patent: Jun. 25, 2024

(54) LAYER BOUNDARY EVOLUTION FOR MACULAR OPTICAL COHERENCE TOMOGRAPHY SEGMENTATION

(71) Applicant: The Johns Hopkins University, Baltimore, MD (US)

(72) Inventors: Jerry L. Prince, Baltimore, MD (US); Aaron Carass, Towson, MD (US); Yihao Liu, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 374 days.

(21) Appl. No.: 17/310,330

(22) PCT Filed: Jan. 31, 2020

(86) PCT No.: PCT/US2020/016171
§ 371 (c)(1),
(2) Date: Jul. 28, 2021

(87) PCT Pub. No.: WO2020/160446
PCT Pub. Date: Aug. 6, 2020

(65) Prior Publication Data
US 2021/0383552 A1    Dec. 9, 2021

Related U.S. Application Data

(60) Provisional application No. 62/800,153, filed on Feb. 1, 2019.

(51) Int. Cl.
| | |
|---|---|
| G06T 7/10 | (2017.01) |
| G06T 7/00 | (2017.01) |
| G06T 7/143 | (2017.01) |
| G16H 30/40 | (2018.01) |
| G16H 50/20 | (2018.01) |
| G16H 50/30 | (2018.01) |

(52) U.S. Cl.
CPC ............ G06T 7/143 (2017.01); G06T 7/0012 (2013.01); G16H 30/40 (2018.01); G16H 50/20 (2018.01);
(Continued)

(58) Field of Classification Search
CPC ................... G06T 7/143; G06T 7/0012; G06T 2207/10101; G06T 2207/20081;
(Continued)

(56) References Cited

U.S. PATENT DOCUMENTS

2009/0125487 A1*   5/2009   Rossi .................... G06F 16/583
2012/0076381 A1   3/2012   Takama
(Continued)

FOREIGN PATENT DOCUMENTS

| CN | 102750693 | * 10/2012 |
| CN | 106650735 | * 12/2016 |
| JP | 2011-194061 A | 10/2011 |

OTHER PUBLICATIONS

Ben-Cohen et al. "Retinal layers segmentation using Fully Convolutional Network in OCT images", RSIP Vision, 2017 (Year: 2017).*
(Continued)

*Primary Examiner* — Qian Yang
(74) *Attorney, Agent, or Firm* — Harrity & Harrity, LLP

(57) ABSTRACT

A device receives a two-dimensional (2-D) image that depicts a cross-sectional view of a retina that includes a macula comprised of layers and boundaries used to segment the layers. The device converts the 2-D image to a standardized format, determines features for voxels included in the 2-D image, and generates, by using a data model to process the features, probability maps that indicate likelihoods of the voxels being in positions within particular boundaries. The device analyzes the probability maps to determine an initial set of boundary positions and to generate directional vectors
(Continued)

that point in directions based on values included in the set of probability maps, determines a final set of boundary positions by performing a layer boundary evolution technique using the directional vectors to refine the initial set of boundary positions, and provides data that identifies the final set of boundary positions for display via an interface.

20 Claims, 13 Drawing Sheets

(52) U.S. Cl.
CPC ... *G16H 50/30* (2018.01); *G06T 2207/10101* (2013.01); *G06T 2207/20081* (2013.01); *G06T 2207/20084* (2013.01); *G06T 2207/20182* (2013.01); *G06T 2207/30041* (2013.01)

(58) Field of Classification Search
CPC . G06T 2207/20084; G06T 2207/20182; G06T 2207/30041; G06T 7/12; G16H 30/40; G16H 50/20; G16H 50/30
See application file for complete search history.

(56) References Cited

U.S. PATENT DOCUMENTS

| | | |
|---|---|---|
| 2012/0328156 A1 | 12/2012 | Nakano et al. |
| 2018/0182082 A1 | 6/2018 | Jia et al. |
| 2018/0263499 A1 | 9/2018 | Sasaki et al. |
| 2021/0133982 A1* | 5/2021 | Bagherinia .......... G06V 10/761 |

OTHER PUBLICATIONS

Mohring et al., "Partitioning Graphs to Speedup Dijkstra's Algorithm", ACM Journal of Experimental Algorithmics, vol. 11, Article No. 2.8, 2006 (Year: 2006).*
Tomasi et al. "Bilateral filtering for gray and color images", IEEE. Sixth International Conference In Computer Vision, pp. 839-846, (1998) (Year: 1998).*
Machine translation for CN 102750693 (Year: 2012).*
Machine translation for CN 106650735 (Year: 2016).*
Liu et al., "Multi-layer fast level set segmentation for macular OCT," 1-20, 2018 IEEE 15th International Symposium on Biomedical Imaging, 2018, pp. 1445-1448.
International Search Report and Written Opinion—PCT/US2020/016171—ISA/KR—dated Jun. 3, 2020.
Extended European Search Report for Application No. EP20748474.2, dated Oct. 19, 2022, 9 pages.
Liu et al., "Layer Boundary Evolution Method for Macular OCT Layer Segmentation," Biomedical Optics Express, Mar. 2019, vol. 10(3), pp. 1064, XP055775964, United States, ISSN: 2156-7085, DOI: 10.1364/BOE.I0.001064.
Liu et al., "Multi-layer Fast Level Set Segmentation for Macular OCT," IEEE International Symposium on Biomedical Imaging, Apr. 2018, pp. 1445-1448, XP033348421, DOI: 10.1109/ISBI.2018.8363844.

* cited by examiner

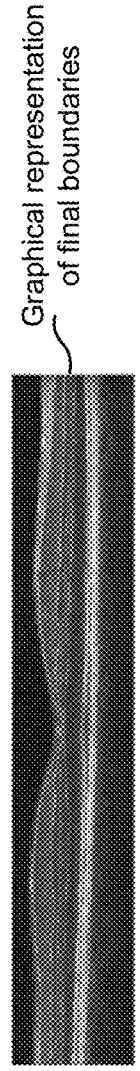

Graphical representation of final boundaries

| Example Rules for Layer Boundary Evolution (LBE) |
|---|
| • If the directional vectors are ⇗⇖, a zero level set location will be calculated as the predicted boundary location |
| • If the directional vectors are ⇘⇙, the surface point moves down: $B^{n+1}(j, k) \leftarrow \text{floor}(B^n(j, k)) - 0.5$ |
| • If the two forces are ⇖⇗, the surface point moves up: $B^{n+1}(j, k) \leftarrow \text{ceil}(B^n(j, k)) + 0.5$ |
| • If the two forces are ⇙⇘, the surface point moves based only on $F_s$ |

160
Determine final set of boundary positions by using the initial set of boundary positions and the set of directional vectors to perform a LBE technique

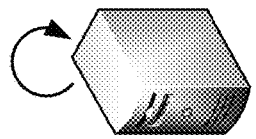

Image Processing Platform

FIG. 1G

LAYER BOUNDARY EVOLUTION FOR MACULAR OPTICAL COHERENCE TOMOGRAPHY SEGMENTATION

RELATED APPLICATIONS

This application is a 371 national stage of PCT Application No. PCT/US2020/016171 filed on Jan. 31, 2020, entitled "LAYER BOUNDARY EVOLUTION FOR MACULAR OPTICAL COHERENCE TOMOGRAPHY SEGMENTATION," which claims priority to U.S. Provisional Patent Application No. 62/800,153, filed on Feb. 1, 2019, which are incorporated by reference herein in their entirety.

GOVERNMENT LICENSE RIGHTS

This invention was made with U.S. Government support under grant R01-EY024655, awarded by the National Institutes of Health (NIH)/National Eye Institute (NEI). The U.S. Government has certain rights in the invention.

BACKGROUND

Optical coherence tomography (OCT) is used to produce high resolution depth images of the retina and is now the standard of care for in-vivo ophthalmological assessment. Additionally, OCT is used for evaluation of neurological disorders such as multiple sclerosis (MS).

SUMMARY

According to some implementations, a method may include receiving, by a device, a two-dimensional (2-D) image that depicts a cross-sectional view of a retina of an eye, wherein the retina includes a macula that includes layers and boundaries that are used to segment the layers. The method may include converting, by the device, the 2-D image to a standardized format, and determining, by the device, a set of features for voxels included in the 2-D image. The method may include generating, by the device and by using a data model to process the set of features, a set of probability maps that indicate likelihoods of the voxels being in positions within particular boundaries, wherein the data model has been trained by using one or more machine learning techniques to analyze a labeled set of 2-D images that depict retinas of eyes and can be combined to depict or form a 3-D model of at least a portion of the retinas. The method may include determining, by the device and by analyzing the set of probability maps, an initial set of boundary positions for the boundaries, and generating, by the device and by analyzing the set of probability maps, a set of directional vectors that point in directions that are based on values included in the set of probability maps. The method may include determining, by the device and by performing a layer boundary evolution (LBE) technique, a final set of boundary positions for the boundaries, wherein performing the LBE technique includes using the set of directional vectors to refine the initial set of boundary positions, and providing, by the device, data that identifies the final set of boundary positions for display via an interface.

According to some implementations, a device may include one or more memories, and one or more processors, operatively coupled to the one or more memories, to receive a data model that has been trained to determine likelihoods of particular voxels being in positions that are within particular boundaries of a layer of a subject's macula, wherein the data model has been trained by using one or more machine learning techniques to analyze a labeled set of 2-D images that depict maculae of eyes. The one or more processors may receive a 2-D image that depicts a cross-sectional view of a macula of an eye, wherein the macula includes layers and boundaries that are used to segment the layers. The one or more processors may convert the 2-D image to a standardized format, and determine a set of features for voxels included in the 2-D image. The one or more processors may generate, by using the data model to process the set of features, a set of probability maps that correspond to the boundaries, wherein the set of probability maps indicate likelihoods of the voxels being in positions within particular boundaries. The one or more processors may determine, by analyzing the set of probability maps, an initial set of boundary positions for the boundaries, and generate, by analyzing the set of probability maps, a set of directional vectors that point in directions that are based on values included in the set of probability maps. The one or more processors may determine a final set of boundary positions for the boundaries by using the set of directional vectors to refine the initial set of boundary positions, determine, after determining the final set of boundary positions, thickness levels of the layers of the macula based on the final set of boundary positions, and perform one or more actions based on the thickness levels of the layers of the macula.

According to some implementations, a non-transitory computer-readable medium may store one or more instructions that, when executed by one or more processors of a device, cause the one or more processors to receive a set of 2-D images that depict a cross-sectional view of a retina of an eye, wherein the retina includes a macula that includes layers and boundaries that are used to segment the layers. The one or more instructions may cause the one or more processors to convert the set of 2-D images to a standardized format, and determine a set of features for voxels included in the set of 2-D images. The one or more instructions may cause the one or more processors to generate, by using a data model to process the set of features, sets of probability maps that indicate likelihoods of the voxels being in positions within particular boundaries, wherein the data model has been trained by using one or more machine learning techniques to analyze a labeled set of 2-D images that depict retinas of eyes. The one or more instructions may cause the one or more processors to determine, for a particular 2-D image of the set of 2-D images, an initial set of boundary positions for the boundaries identified within the particular 2-D image, wherein the initial set of boundary positions are determined by using a shortest path technique to analyze a set of probability maps, of the sets of probability maps, that are associated with the particular 2-D image. The one or more instructions may cause the one or more processors to generate, by analyzing the set of probability maps, a set of directional vectors that point in directions that are based on values included in the set of probability maps, and determine, by performing an LBE technique, a final set of boundary positions for the boundaries identified within the particular 2-D image, wherein performing the LBE technique includes using the set of directional vectors to refine the initial set of boundary positions. The one or more instructions may cause the one or more processors to determine whether thickness levels of the layers are indicative of a disease based on the final set of boundary positions, and provide, for display via an interface, at least one of: data that identifies the final set of boundary positions, or an indication of whether the thickness levels of the layers are indicative of a severity of the disease.

BRIEF DESCRIPTION OF THE DRAWINGS

FIGS. 1A-1H are diagrams of one or more example implementations described herein.

DETAILED DESCRIPTION

Figure 1A:
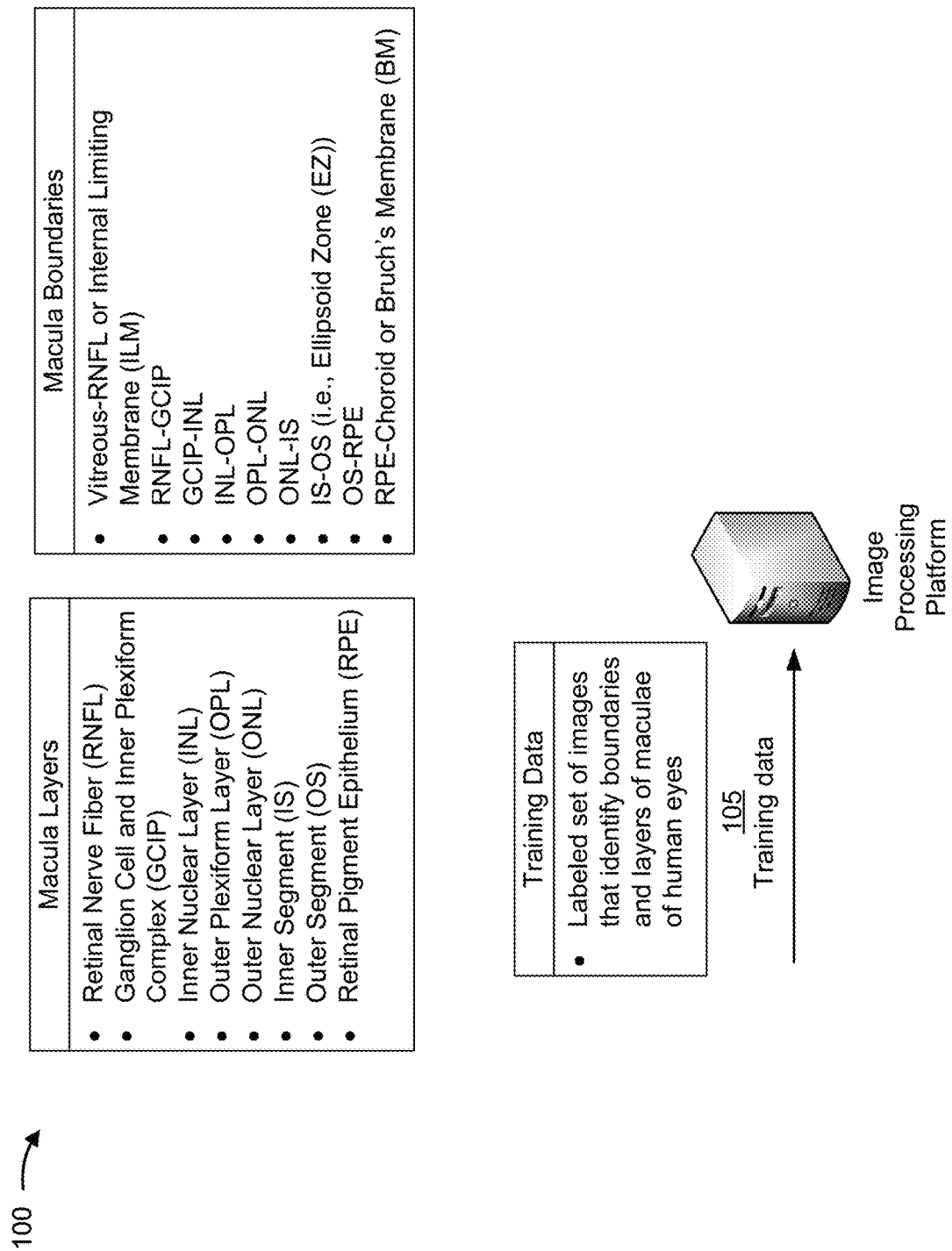

The following detailed description of example implementations refers to the accompanying drawings. The same reference numbers in different drawings may identify the same or similar elements.

Optical coherence tomography (OCT) may be used for evaluation of retinal and neurological disorders, such as multiple sclerosis (MS). For example, to determine whether a patient has MS, an ophthalmological assessment may be performed that includes measuring a thickness of a set of cellular layers (referred to herein as layers) of a macula of the patient's eye. The thickness may serve as an indicator of whether the patient has MS and/or a severity of MS. For example, an individual with MS may have reduced thickness at one or more layers of the macula (relative to a healthy patient). Additionally, or alternatively, one or more layers of the macula of an individual with a relatively more severe case of MS may be thinner than corresponding layers of an individual with a relatively less severe case of MS. Accordingly, comparisons of separate scans of a macula can be used to determined whether a patient's MS is worsening, steadying, and/or improving.

To measure the thickness, an imaging system may be used to capture images of the eye. In this case, the imaging system may emit a beam of light into tissues of the eye and may detect reflected or back-scattered light from the tissues. This reflected light will interfere with the beam of light and may be used to create a reflectivity profile that is then used to generate a collection of amplitude scans (A-scans). The A-scans may be combined to form 2-D brightness-mode scans (B-scans) that are collectively referred to as a three-dimensional (3-D) OCT volume. According to some implementations, multiple 2-D cross-sectional images of the retina can be combined, using any suitable process, to form a 3-D image of the retina or eye, according to the processes described herein.

Several techniques exist for identifying the thickness of the set of layers of the macula. For example, manual segmentation involves having a team of human experts analyze the OCT volume to manually identify boundaries used to segment the set of layers of the macula. This solution is time consuming and subjective. A number of other techniques involve automatic segmentation, whereby software is able to identify the boundaries. For example, some automatic segmentation techniques may generate models that identify boundaries using a shortest path technique, a technique using active contours, a technique using level sets, and the like.

However, many of these automatic segmentation techniques are unable to achieve a sub-voxel level of accuracy when identifying the layers. Because of the level of granularity that goes into identifying boundaries used to segment layers of a macula, even slightly inaccurate identifications of the boundaries may cause inaccurate test results (e.g., a test result indicating that the patient has MS and/or a severity of MS, a test result indicating that the patient does not have MS and/or is less likely to have MS, and/or the like) and/or inaccurate analyses of treatment associated with an analyzed disease (e.g., whether treatment applied between scans has been effective in treating or slowing down the advancement of MS throughout the patient) associated with characteristics of one or more layers of the macula. Furthermore, devices implementing one or more of these automatic segmentation techniques waste a significant amount of resources (e.g., processing resources, network resources, and/or the like) by inefficiently processing the OCT volume (e.g., relative to one or more solutions described herein).

Some implementations described herein provide an image processing platform to use a layer boundary evolution (LBE) technique to determine boundary positions for boundaries used to segment a set of layers of a macula, where the boundary positions are determined with sub-voxel precision. For example, an imaging system may capture a set of 2-D images (e.g., B-scans) of the macula and may provide the set of 2-D images to the image processing platform. In this case, the image processing platform may convert the 2-D images to a standardized format and may determine a set of features for voxels included in the 2-D images.

Additionally, the image processing platform may generate a set of probability maps that indicate likelihoods of the voxels being part of particular boundaries. For example, the image processing platform may have trained a data model (as described further herein) and may generate the set of probability maps by using the data model to process the 2-D images that have been converted to the standardized format. In this case, the image processing platform may, based on an analysis of the set of probability maps, determine an initial set of boundary positions for the boundaries that are used to segment the set of layers of the macula, and may generate a set of directional vectors that may be used to refine the initial set of boundary positions. Furthermore, the image processing platform may perform the LBE technique to determine a final set of boundary positions for the boundaries. For example, the image processing platform may determine the final set of boundary positions by using the set of directional vectors to refine the initial set of boundary positions. The final set of boundary positions may identify positions within a B-scan of specific voxels and/or positions within the specific voxels, such that the final set of boundary positions are determined with voxel or sub-voxel precision. Additionally, the image processing platform may provide data that identifies the final set of boundary positions for display via an interface (e.g., such that a doctor may view the final set of boundaries, measure thickness of each layer, and determine whether a patient has a neurological disorder, such as MS, and/or whether the neurological disorder has advanced, accelerated, or steadied).

In this way, the image processing platform is able to identify the boundaries that segment the set of layers of the macula with voxel or sub-voxel precision. Furthermore, the image processing platform is able to identify the boundaries while making an efficient and effective use of resources (e.g., processing resources, network resources, and/or the like). For example, by using Gaussian filtering to determine the set of directional vectors (e.g., without calculating curvature), the image processing platform conserves resources and reduces computational time relative to an inferior solution. Additionally, by using vector field convolution (VFC) to determine the set of directional vectors, the image processing platform reduces a utilization of resources and improves computational time relative to solutions utilizing gradient vector flow techniques. Moreover, by using LBE, the image processing platform identifies boundary positions with voxel or sub-voxel precision, which improves accuracy of test results, thereby conserving resources that might otherwise be used to generate less accurate or inaccurate test results.

Figure 1B:
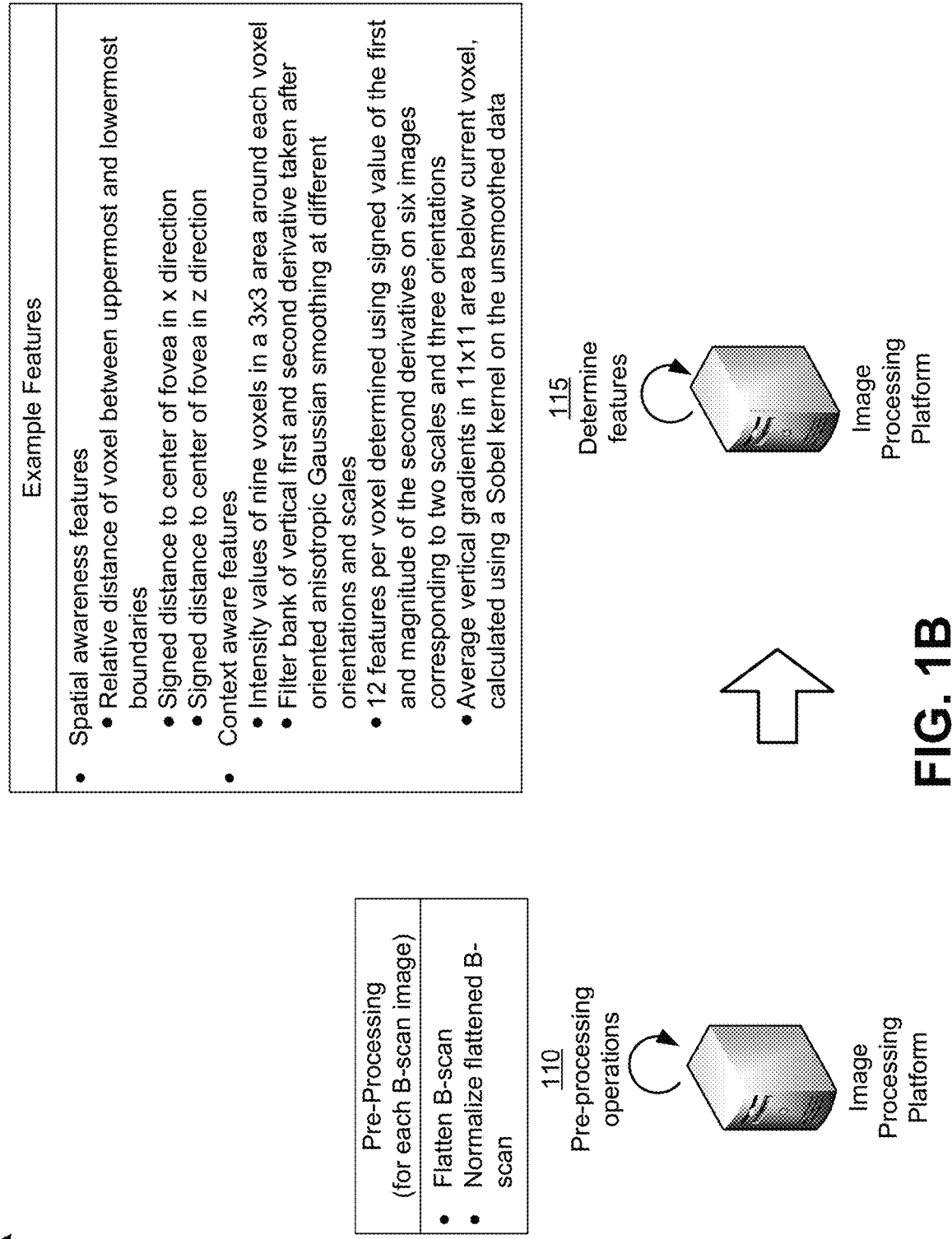
Figure 1C:
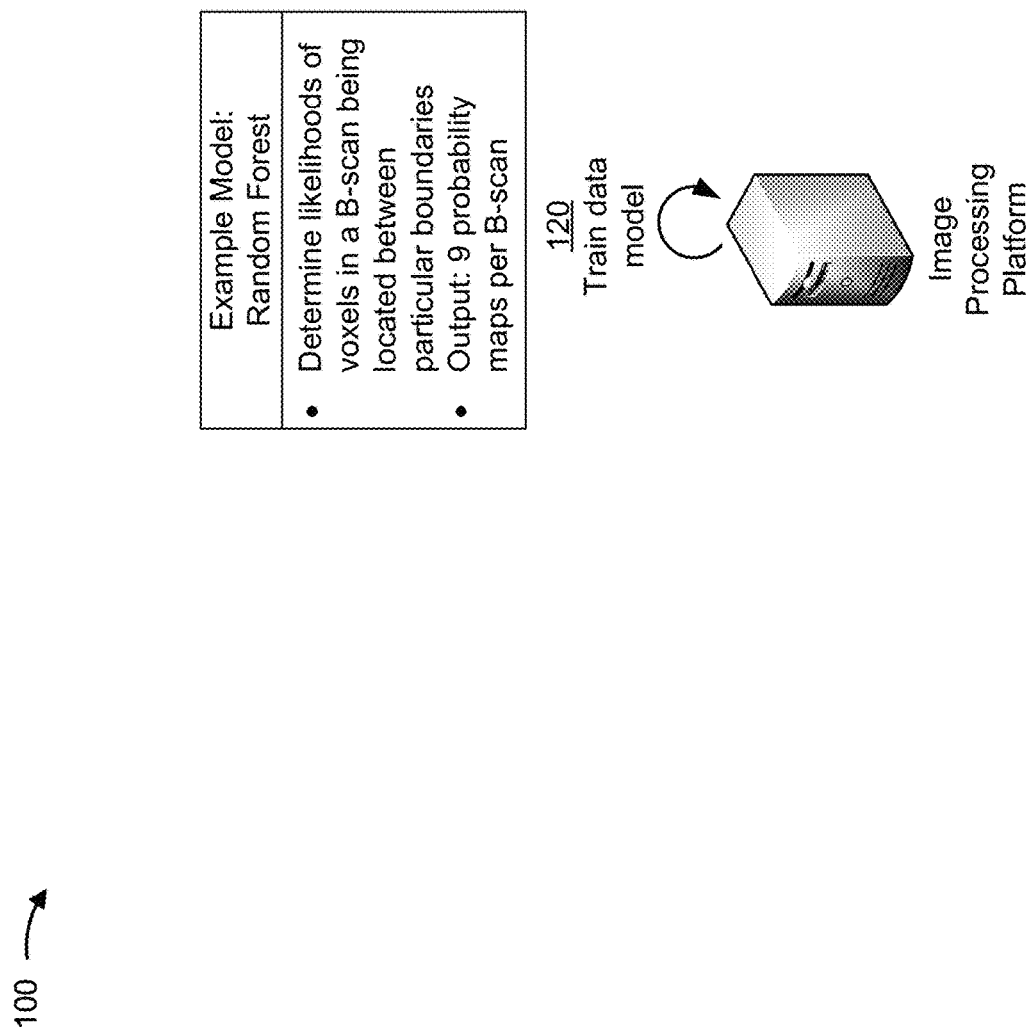

FIGS. 1A-1H are diagrams of one or more example implementations 100 described herein. Example implementations 100 may include an image processing platform, a imaging system, and a user device. As shown in FIGS. 1A-1C, the image processing platform may train a data model to predict likelihoods of voxels within a 2-D image (e.g., a B-scan) being within particular boundaries that are used to segment layers of maculae of human eyes. As shown in FIGS. 1D-1H, the image processing platform may receive a set of B-scans that depict a macula of a human eye, may use the data model and a layer boundary evolution (LBE) technique to determine boundaries for a set of layers of the macula, and may use data that identifies the boundaries to complete a test that is indicative of whether a patient has an eye disorder or a neurological disorder, such as multiple sclerosis (MS).

As shown in FIG. 1A, and by reference number 105, the image processing platform may receive training data that may be used to train the data model. For example, the image processing platform may receive, from a data storage device, training data that includes a labeled set of images of maculae of human eyes. The labeled set of images may include data that identifies layers of the maculae and data that identifies boundaries that are used to segment the set of layers. In some implementations, the image processing platform may receive unlabeled training data and labeled test data, such that the unlabeled training data and the labeled test data may be used to train the data model in a manner described further herein.

As shown, the set of layers may include a retinal nerve fiber (RNFL) layer, a ganglion cell and inner plexiform complex (GCIP) layer, an inner nuclear layer (INL), an outer plexiform layer (OPL), an outer nuclear layer (ONL), an inner segment (IS) layer, an outer segment (OS) layer, and a retinal pigment epithelium (RPE) layer. The set of boundaries may be used to define the layers (e.g., by identifying a line that separates two neighboring layers). The set of boundaries may include a vitreous-RNFL or internal limiting membrane (ILM) boundary, an RNFL-GCIP boundary, a GCIP-INL boundary, an INL-OPL boundary, an OPL-ONL boundary, an ONL-IS boundary, an OS-RPE boundary, and an RPE-Choroid or Bruch's membrane (BM) boundary.

In this way, the image processing platform receives training data that may be used to train the data model.

As shown in FIG. 1B, and by reference number 110, the image processing platform may perform one or more preprocessing operations to convert the training data to a standardized format. For example, the image processing platform may flatten the set of B-scans and may normalize the set of B-scans that have been flattened. This will allow the image processing platform to train the data model using images that share a common format, file type, and/or the like.

In some implementations, the image processing platform may flatten a B-scan. For example, the image processing platform may analyze the B-scan to estimate positions (i.e., locations within the B-scan) of outermost boundaries of the set of layers (e.g., the ILM and the BM). In this case, the image processing platform may filter the B-scan using a Gaussian smoothing technique. For example, the image processing platform may use a configured Gaussian smoothing kernel (e.g., using three voxels or a similar number of voxels) to determine derivatives for a set of amplitude scans (A-scans) within the B-scan. More specifically, the Gaussian smoothing technique may be used to compute a different set of vector fields for that boundary positions, thereby enforcing a smoothness between the layers. In this way, an initial set of boundary positions can be identified using VFC and/or Gaussian smoothing.

Continuing with the example, positions of the outermost boundaries in a given A-scan may be identified as the positions that have the largest positive and negative derivative values, respectively. Additionally, the image processing platform may determine error values by comparing estimated positions of the outermost boundaries with a median filtered surface. A voxel may be filtered if a position of the voxel is not within a threshold distance of the median filtered surface. A voxel may be filtered at a given position by being replaced with an interpolated voxel. In this case, the image processing platform may flatten the B-scan by vertically shifting each A-scan based on the estimated positions that have been filtered.

In some implementations, the image processing platform may normalize a B-scan that has been flattened. For example, the image processing platform may normalize the B-scan by identifying or determining a set of intensity values associated with voxels within the B-scan and by normalizing the set of intensity values.

As shown by reference number 115, the image processing platform may determine a set of features that may be used to train the data model. For example, the image processing platform may use one or more feature determination techniques to determine a set of features for the set of voxels included in the training data. The one or more feature determination techniques may include a technique using a random forest (RF), a technique using a support vector machine (SVM), a boosting technique, a deep neural network, and/or the like.

The set of features may include a first subset of features that provide spatial awareness and a second subset of context-aware features. The first subset of features may include a feature that identifies a relative distance of each voxel (e.g., along an A-scan) between the outermost boundaries identified above, a feature that identifies a signed distance to a center of a fovea in an x direction, a feature that identifies a signed distance to the center of the fovea in a z direction, and/or the like. The second subset of features may include a feature that identifies intensity values for an area around each voxel (e.g., intensity values of a 3×3 voxel region around a particular target voxel), a feature that identifies an average vertical gradient in an area within the B-scan (e.g., an 11×11 voxel area), and/or the like. These features may assist the image processing platform in determining whether particular voxels are within (i.e., part of) particular boundaries.

In this way, the image processing platform is able to determine a set of features that may be used to train the data model.

As shown in FIG. 1C, and by reference number 120, the image processing platform may train the data model. For example, the image processing platform may train the data model by using one or more machine learning techniques and the set of features to analyze the set of B-scans that have been pre-processed. In this case, the image processing platform may train the data model to be able to receive a B-scan as an input and to generate probability maps that indicate likelihoods of voxels in the B-scan being in positions within particular boundaries. A probability map may be an array of values that, for each voxel of a B-scan, indicates a likelihood of the voxel being within a particular boundary. Additionally, a number of probability maps that are generated for a given B-scan may correspond to a number of boundaries (e.g., if there are nine boundaries, the image processing platform may generate nine probability maps). Furthermore, the probability maps may be used to determine initial boundary positions for the boundaries, which may be used in conjunction with layer boundary evolution (LBE) to determine final boundary positions, as will be described further herein.

In some implementations, the image processing platform may train a random forest. For example, the image processing platform may train a random forest using the set of features determined above. In this case, the image processing platform may process the set of B-scans and may generate probability maps that indicate likelihoods of voxels being within particular boundaries.

In this way, the image processing platform is able to train the data model to generate probability maps that may be used to determine initial boundary positions for the boundaries. This may allow the image processing platform to perform the LBE technique to determine the final boundary positions, as described further herein.

Figure 1D:
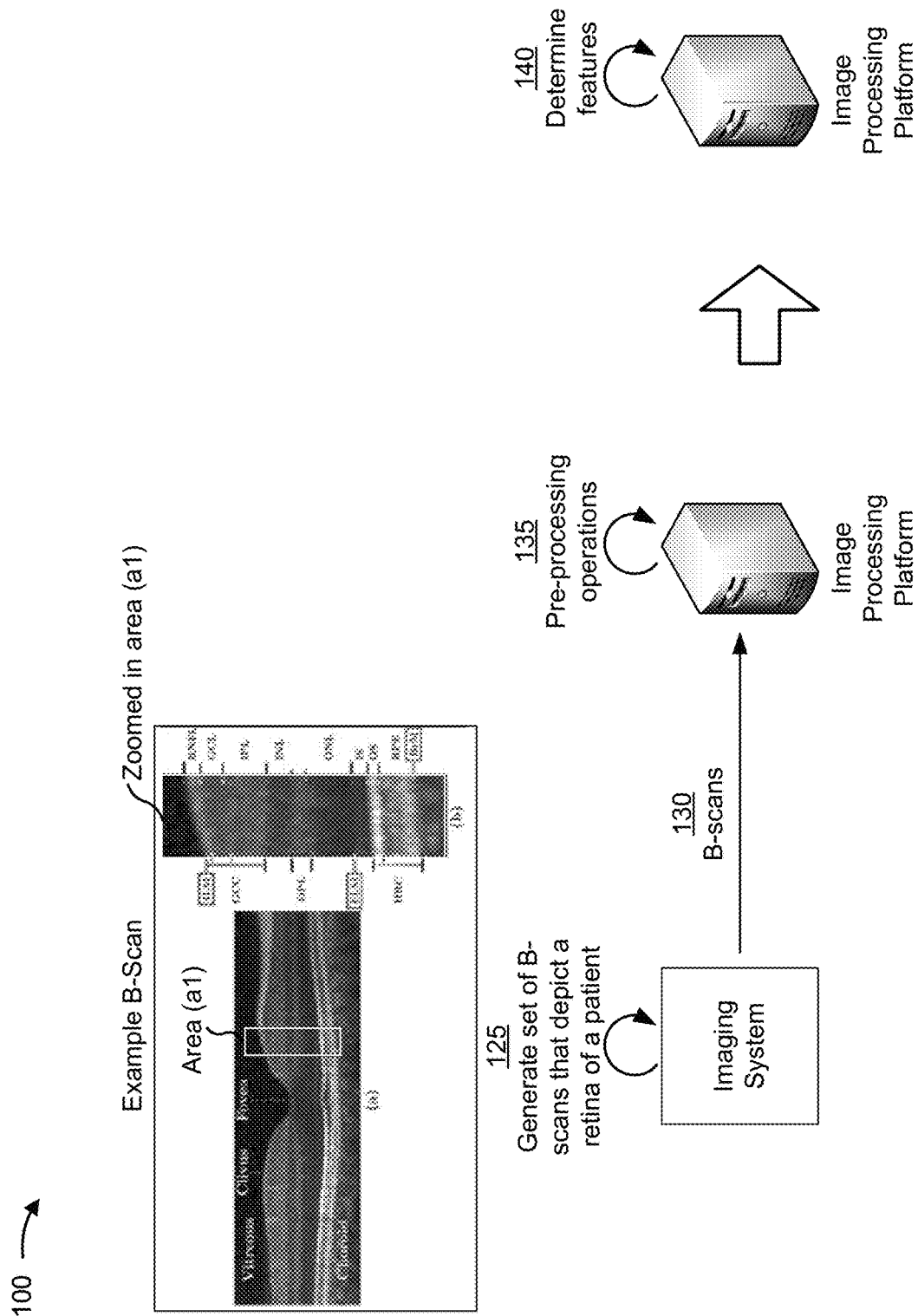

As shown in FIG. 1D, and by reference number 125, the imaging system may generate a set of B-scans that depict a macula of an eye of a patient that is being tested for an eye disorder or a neurological disorder. For example, the imaging system may be positioned in a manner that allows a lens of an image capturing component to be zoomed in on the eye of the patient. In this case, the imaging system may take a series of images of the eye to generate the set of B-scans.

As shown by reference number 130, the imaging system may provide the set of B-scans to the image processing platform. For example, the imaging system may provide the set of B-scans to the image processing platform using a communication interface, such as an application programming interface (API) or a similar type of interface. In some implementations, the imaging system may provide the set of B-scans to one or more intermediary devices which may provide the set of B-scans to the image processing platform.

As shown by reference number 135, the image processing platform may perform one or more pre-processing operations. For example, the image processing platform may perform one or more pre-processing operations to convert the set of B-scans to a standardized format, as described elsewhere herein.

As shown by reference number 140, the image processing platform may determine a set of features for voxels included in the set of B-scans. For example, the image processing platform may determine a set of features that may be used as an input to the data model by using one or more feature determination techniques to analyze the set of B-scans that have been standardized, as described elsewhere herein.

In this way, the image processing platform is able to receive a set of B-scans and to determine a set of features associated with the set of B-scans that may be used as an input to the data model.

Figure 1E:
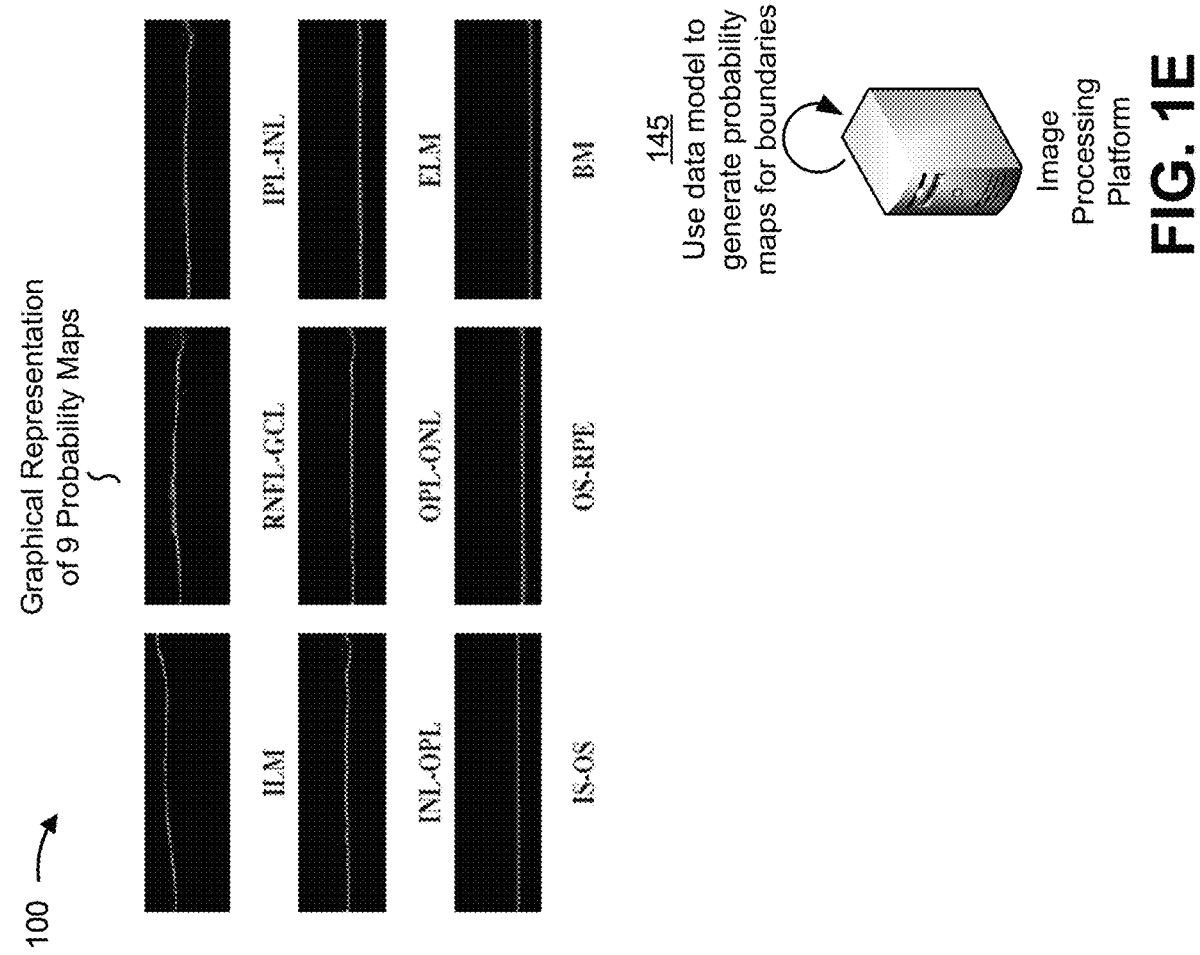

As shown in FIG. 1E, and by reference number 145, the image processing platform may use the data model to generate a set of probability maps. For example, the image processing platform may use the data model to generate a set of probability maps that indicate likelihoods of the voxels being in positions within a particular boundary. In this case, the image processing platform may, for a given B-scan, generate a probability map for each boundary of the boundaries used to segment the set of layers of the macula. The image processing platform may generate these probability maps for each B-scan of the set of B-scans.

In the example shown, the image processing platform may, for a particular B-scan, generate a probability map for the ILM boundary. In this example, the probability map may be an array of values that identifies, for each voxel in the particular B-scan, a likelihood of each voxel being within the ILM boundary. Additionally, the values may be set to values between zero and one, where a value of zero is associated with a lowest possible likelihood of a voxel being within the ILM boundary and a value of one is associated with a highest possible likelihood of a voxel being within the ILM boundary. As shown, the probably map may include values for a number N of voxels, and may include, for voxel number 153, a value of 0.88, which, relative to other voxels, is a highest possible likelihood of voxel number 153 being within the IML boundary.

In this way, the image processing platform is able to use a data model to generate a set of probability maps for the boundaries.

Figure 1F:
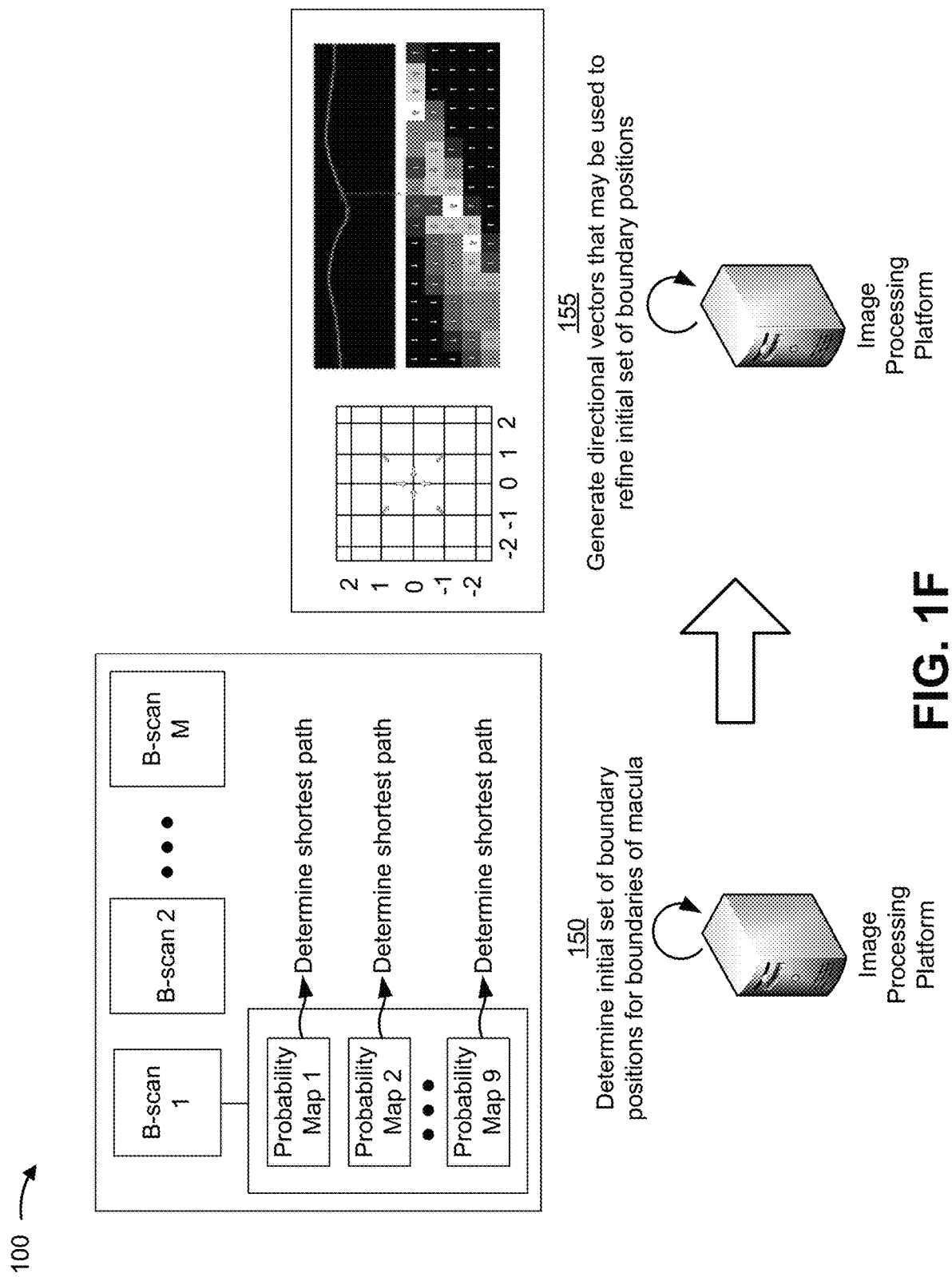

As shown in FIG. 1F, and by reference number 150, the image processing platform may determine an initial set of boundary positions for boundaries of the macula. For example, the image processing platform may determine an initial set of boundary positions by using a shortest path technique to analyze the set of probability maps. In this case, the image processing platform may use the shortest path technique to determine the initial set of boundary positions for each boundary (i.e., each probability map) of a set of probability maps associated with a B-scan. The image processing platform may repeat this process for each B-scan of the set of B-scans.

In some implementations, the image processing platform may use the shortest path technique to determine an initial set of boundary positions for a boundary within a first B-scan. For example, a probability map may indicate likelihoods of each voxel being within the boundary, and the image processing platform may determine an initial range of boundary positions based on the likelihoods identified in the probably map.

As shown by reference number 155, the image processing platform may generate a set of directional vectors that may be used to refine the initial set of boundary positions. For example, the initial set of boundary positions may be viewed as a superset of candidate boundary positions that include actual boundary positions, and the image processing platform may generate a set of directional vectors that may be used to locate the actual boundary positions within the initial set of boundary positions. In this case, the image processing platform may generate a set of directional vectors such that each voxel within a B-scan is given a particular directional vector.

In some implementations, the set of directional vectors may be an array that includes values that are either one or zero, whereby a value of one reflects a first direction (e.g., toward a top-most portion of a B-scan) and a value of zero reflects a second direction (e.g., toward a bottom-most portion of the B-scan). Consequently, if a voxel is located below a boundary, the voxel may be given a directional value of one, which may represent the first direction and indicate that the boundary is located somewhere above the voxel.

In some implementations, the image processing platform may generate a set of directional vectors using a vector field convolution (VFC) technique. For example, the image processing platform may be configured with a vector field kernel and may convolve the vector field kernel along different portions of a probability map. In this case, the vector field kernel may be applied to each voxel, of a set of voxels within a B-scan, and may be used to determine a vector field whose vectors point toward a highest likelihood of being within a particular boundary.

In this way, the image processing platform is able to generate a set of directional vectors that may be used when performing the LBE technique to refine the initial set of boundary positions, as described below.

As shown in FIG. 1G, and by reference number 160, the image processing platform may determine the final set of boundary positions by using the initial set of boundary positions and the set of directional vectors to perform the LBE technique. For example, the image processing platform may, while performing the LBE technique, apply a set of rules to the initial set of boundary positions and the set of directional vectors to determine a manner in which to refine the initial set of boundary positions.

The set of rules may include a first rule indicating that a specific boundary position is to be added to the final set of boundary positions if two vertically-aligned directional vectors are pointed toward each other in opposite directions, a second rule indicating that the specific boundary position is not to be added to the final set of boundary positions if the two vertically-aligned directional vectors are pointed in a uniform (or same) direction, a third rule indicating that a smoothing technique is to be used when considering the specific boundary position if the two vertically-aligned directional vectors are pointed away from each other in opposite directions, and/or the like.

As an example, the image processing platform may, for a particular pair of vertically-aligned neighboring voxels that have been assigned directional vectors, identify a direction in which the directional vectors are pointing. If the directional vectors are pointing toward each other in an opposite direction, then the image processing platform may select a boundary position between the neighboring voxels as being part of a final set of boundary positions. If the directional vectors are pointed in a uniform direction, then the image processing platform will not select the boundary position to be included in the final set of boundary positions. In this case, the uniform direction may be used to identify a next pair of vertically-aligned voxels that are to be considered. If the directional vectors are pointed away from each other in opposite directions, then the image processing platform may apply a smoothing technique to select a specific boundary position. For example, in this case, the image processing platform might consider nearby boundary positions of neighboring voxels in a horizontal direction and may select a boundary position that would connect to the already-selected boundary positions of the neighboring voxels in the horizontal direction.

According to some implementations, the image processing platform may maintain the boundaries according to a set of constraints associated with and/or defined by an order (e.g., a preconfigured order or predefined order) of the layers. For example, the image processing platform may determine the order of the layers to constrain the boundaries relative to the layers to prevent reordering of the layers (e.g., because the layers of the macula are constant or always the same). Accordingly, if measured forces for a particular voxel would cause the image processing platform to invert a set of layers in a B-scan (e.g., due to an error or anomaly), the image processing platform would detect an interpreted change in the boundary order within the B-scan and prevent the boundary order from being changed (e.g., by moving the boundaries of a particular layer as close as possible without changing the order of the layers (and/or boundaries between layers)). In this way, the image processing platform may detect any errors and/or anomalies that might cause an inversion of one or more layers depicted in the B-scan, and prevent the inversion.

By applying the set of rules to each voxel, the image processing platform is able to determine the final set of boundary positions for the boundaries of the set of layers of the macula. In some implementations, the final set of boundary positions for the boundaries of the set of layers are interpolated to be within a particular voxel (e.g., as opposed to between a pair of voxels) based on interpolating (or combining) forces of adjacent pixels within the B-scan. For example, for opposing forces that are directed toward each other within a particular pair of adjacent voxels within a column, the image processing platform may interpolate the forces to determine the boundary as being within one of the two voxels. As described herein, when a boundary is determined to be within a voxel, the boundary is considered to be between sub-voxels of the voxel, thus enabling a determination of the boundary with sub-voxel precision. More specifically, if an initial boundary is determined to be between two adjacent voxels according to the opposing forces, the boundary may be determined to be through (or between sub-voxels) of the voxel that has a force with a lesser magnitude (e.g., because the force of the voxel with the higher magnitude pushes the boundary into the other voxel). On the other hand, if the magnitudes of the forces of the pair of adjacent voxels are equal, opposite, and pointing toward each other, the image processing platforms determines that the boundary of the layers is between the voxels.

In this way, based on applying the set of rules to each voxel and/or pairs of voxels of a B-scan, the image processing platform may determine, with improved accuracy (e.g., to a sub-voxel level) a corresponding position of a boundary between layers of the macula.

Figure 1H:
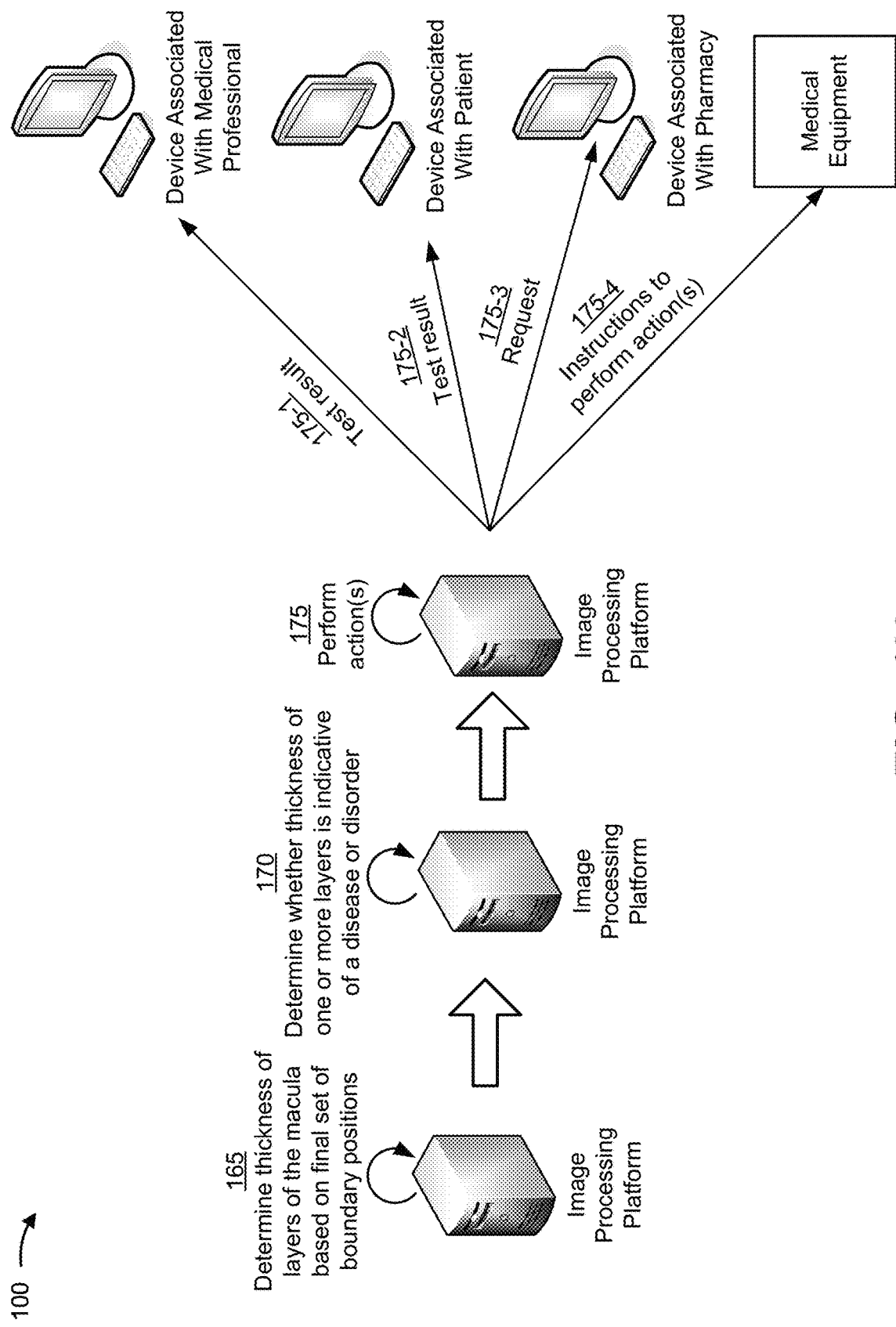

As shown in FIG. 1H, and by reference number 165, the image processing platform may determine a thickness of layers of the macula based on the final set of boundary positions. For example, the image processing platform may measure a distance between neighboring boundaries to determine a thickness of each layer of the macula.

As shown by reference number 170, the image processing platform may determine whether the thickness of one or more layers is indicative of a disease or neurological disorder. For example, the image processing platform may be configured with a set of measured thicknesses of particular layers of a macula as would be found in both healthy patients and patients who have a disease or a neurological disorder. In this case, the image processing platform may compare the set of measured thicknesses to the thickness of the set of layers of the macula that is being analyzed to determine whether one or more of the set of layers has a thickness that may be indicative of disease or neurological disorder.

As shown by reference number 175, the image processing platform may perform one or more actions. For example, the image processing platform may, based on determining whether the thickness of the one or more layers is indicative of a disease or neurological disorder, perform a first set of one or more actions to cause test results to be displayed on an interface of a device associated with a medical professional, perform a second set of one or more actions to cause a device associated with the patient to be provided with the test results, perform a third set of one or more actions to cause a prescription to be ordered for the patient, perform a fourth set of one or more actions to cause medical equipment to perform a procedure on the patient, and/or the like, as each described below.

As shown by reference number 175-1, the image processing platform may provide, to a device associated with a medical professional, test results data. For example, the image processing platform may generate the test results data based on determining whether the thickness of one or more layers of the patient's macula is indicative of a disease or disorder. In this case, the image processing platform may provide the rest results data to the device associated with the medical professional (e.g., using an API or a similar type of interface). This may allow the medical professional to review the test results data and to make a medical recommendation for the patient.

As shown by reference number 175-2, the image processing platform may provide the test results data to a device (or account) associated with a patient. For example, the image processing platform may provide the test results data to the device (or account) associated with the patient using an API or a similar type of interface. This may notify the patient of the test results and, in some cases, may instruct the patient on a next step (e.g., to begin a treatment plan, and/or the like).

As shown by reference number 175-3, the image processing platform may provide, to a device associated with a pharmacy, a request for a prescription medication that may be used to treat or cure a disease or disorder. For example, the image processing platform may generate the request by populating a form with patient data and may use an API or similar type of interface to provide the request to the device associated with the pharmacy. In this case, the request may also be provided to the device associated with the medical professional (e.g., to allow the medical professional to sign off on the prescription medication).

As shown by reference number 175-4, the image processing platform may provide, to particular medical equipment, a set of instructions to perform one or more actions. For example, if the patient is found to have a likelihood of a disease or disorder and/or a particular severity associated with the disease or disorder, there may be immediate treatment available. In this case, the image processing platform may generate a set of instructions for a machine that is able to perform one or more aspects of the treatment to permit the machine to perform the treatment. As an example, a robotic arm may be tasked with performing a procedure on the patient's eye, and the image processing platform may instruct the robotic arm to perform the procedure.

In this way, the image processing platform is able to identify the boundaries that segment the set of layers of the macula with voxel or sub-voxel precision. Furthermore, the image processing platform is able to identify the boundaries while making an efficient and effective use of resources (e.g., processing resources, network resources, and/or the like).

As indicated above, FIGS. 1A-1H are provided merely as one or more examples. Other examples may differ from what is described with regard to FIGS. 1A-1H. For example, there may be additional devices and/or networks, fewer devices and/or networks, different devices and/or networks, or differently arranged devices and/or networks than those shown in FIGS. 1A-1H. Furthermore, two or more devices shown in FIGS. 1A-1H may be implemented within a single device, or a single device shown in FIGS. 1A-1H may be implemented as multiple and/or distributed devices. Additionally, or alternatively, a set of devices (e.g., one or more devices) of example implementations 100 may perform one or more functions described as being performed by another set of devices of example implementations 100.

Figure 2:
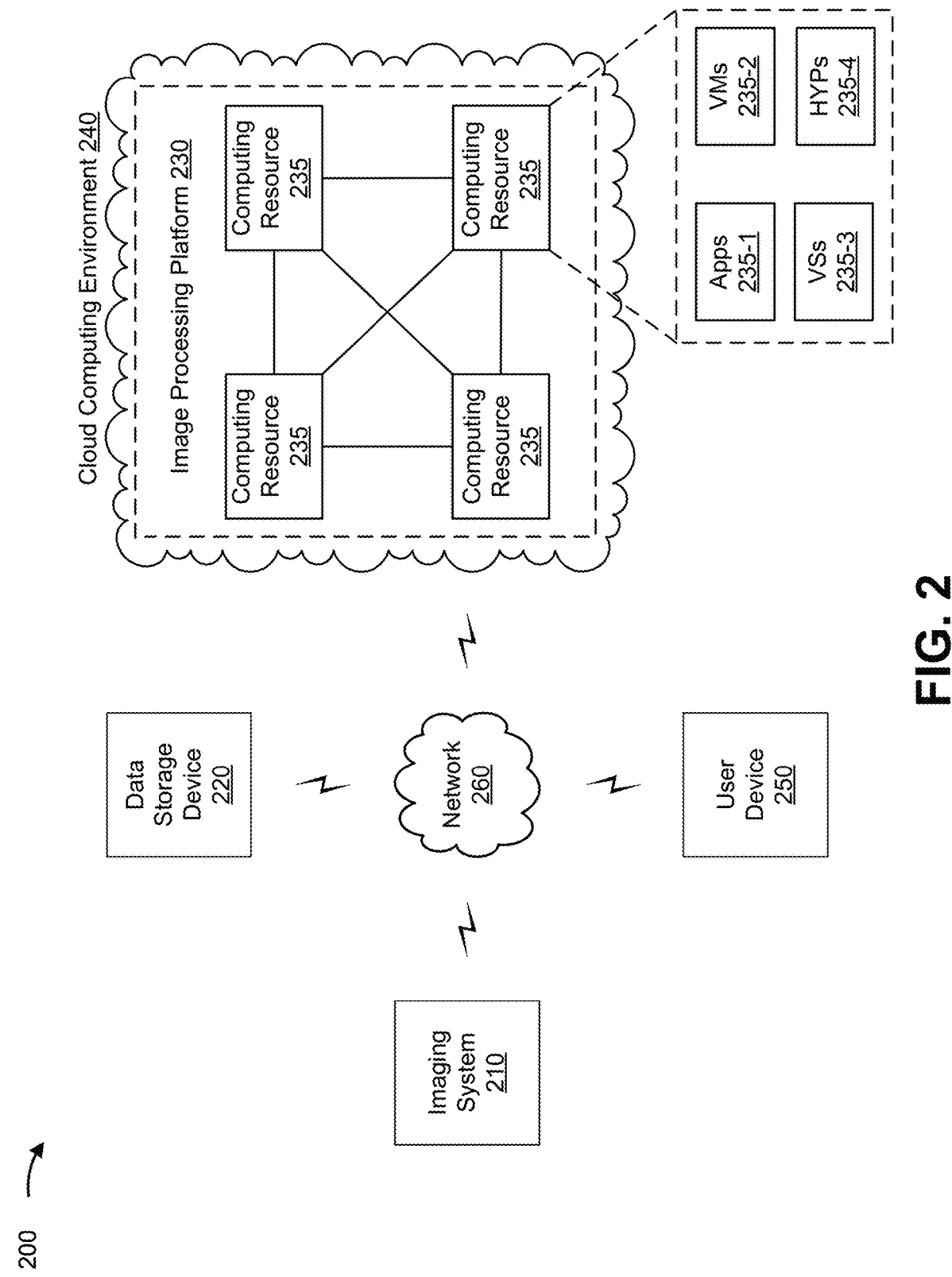
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include an imaging system 210, a data storage device 220, an image processing platform 230 in a cloud computing environment 240 that includes a set of computing devices 235, a user device 250, and a network 260. Devices of environment 200 may interconnect via wired connections, wireless connections, or a combination of wired and wireless connections.

Imaging system 210 includes one or more devices capable of receiving, storing, generating, determining, and/or providing information associated with a set of images (e.g., a set of B-scans). For example, imaging system 210 may include one or more components of a scanning device that is capable of performing OCT. Additionally, or alternatively, the imaging system may one or more of a magnetic resonance imaging (MM) device, an X-ray computed tomography (CT) scan device, a positron emission tomography (PET) device, an ultrasound imaging (USI) device, a photoacoustic imaging (PAI) device, and/or a similar type of device. In some implementations, imaging system 210 may generate and provide image processing platform 230 with a set of B-scans, as described herein.

Data storage device 220 includes one or more devices capable of receiving, storing, generating, determining, and/or providing information associated with training data (e.g., a labeled set of B-scans). For example, data storage device 220 may include a server device or a group of server devices. In some implementations, data storage device 220 may store training data that may be used to train a data model, as described elsewhere herein.

Image processing platform 230 includes one or more devices capable of receiving, storing, generating, determining, and/or providing information associated with an optical coherence tomography (OCT) volume. For example, image processing platform 230 may include a server device (e.g., a host server, a web server, an application server, etc.), a data center device, or a similar device. In some implementations, image processing platform 230 may receive training data from data storage device 220. In some implementations, image processing platform 230 may receive a set of B-scans from imaging system 210. In some implementations, image processing platform 230 may determine a final set of boundary positions for layers of a macula and may use the final set of boundary positions to determine a thickness of the layers, as described elsewhere herein. In some implementations, image processing platform 230 may interact with user device 250 to perform one or more actions described herein.

In some implementations, as shown, image processing platform 230 may be hosted in cloud computing environment 240. While implementations described herein describe image processing platform 230 as being hosted in cloud computing environment 240, in some implementations, image processing platform 230 might not be cloud-based (i.e., may be implemented outside of a cloud computing environment) or may be partially cloud-based.

Cloud computing environment 240 includes an environment that hosts image processing platform 230. Cloud computing environment 240 may provide computation, software, data access, storage, etc., services that do not require end-user knowledge of a physical location and configuration of system(s) and/or device(s) that hosts image processing platform 230. As shown, cloud computing environment 240 may include a group of computing resources 235 (referred to collectively as "computing resources 235" and individually as "computing resource 235").

Computing resource 235 includes one or more personal computers, workstation computers, server devices, or another type of computation and/or communication device. In some implementations, computing resource 235 may host image processing platform 230. The cloud resources may include compute instances executing in computing resource 235, storage devices provided in computing resource 235, data transfer devices provided by computing resource 235, and/or the like. In some implementations, computing resource 235 may communicate with other computing resources 235 via wired connections, wireless connections, or a combination of wired and wireless connections.

As further shown in FIG. 2, computing resource 235 may include a group of cloud resources, such as one or more applications ("APPs") 235-1, one or more virtual machines ("VMs") 235-2, virtualized storage ("VSs") 235-3, one or more hypervisors ("HYPs") 235-4, and/or the like.

Application 235-1 may include one or more software applications that may be provided to or accessed by imaging system 210, data storage device 220, and/or user device 250. Application 235-1 may eliminate a need to install and execute the software applications on these devices. For example, application 235-1 may include software associated with image processing platform 230 and/or any other software capable of being provided via cloud computing environment 240. In some implementations, one application 235-1 may send/receive information to/from one or more other applications 235-1, via virtual machine 235-2.

Virtual machine 235-2 may include a software implementation of a machine (e.g., a computer) that executes programs like a physical machine. Virtual machine 235-2 may be either a system virtual machine or a process virtual machine, depending upon use and degree of correspondence to any real machine by virtual machine 235-2. A system virtual machine may provide a complete system platform that supports execution of a complete operating system. A process virtual machine may execute a single program and may support a single process. In some implementations, virtual machine 235-2 may execute on behalf of another device (e.g., imaging system 210, data storage device 220, and/or user device 250, and/or the like), and may manage infrastructure of cloud computing environment 240, such as data management, synchronization, or long-duration data transfers.

Virtualized storage 235-3 may include one or more storage systems and/or one or more devices that use virtualization techniques within the storage systems or devices of computing resource 235. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 235-4 may provide hardware virtualization techniques that allow multiple operating systems (e.g., "guest operating systems") to execute concurrently on a host computer, such as computing resource 235. Hypervisor 235-4 may present a virtual operating platform to the guest operating systems and may manage the execution of the guest operating systems. Multiple instances of a variety of operating systems may share virtualized hardware resources.

User device 250 includes one or more devices capable of receiving, generating, storing, processing, and/or providing information associated with a test result. For example, user device 250 may include a device or machine, such as a mobile phone (e.g., a smart phone, a radiotelephone, and/or the like), medical equipment, a laptop computer, a tablet computer, a handheld computer, a server computer, a gaming device, a wearable communication device (e.g., a smart wristwatch, a pair of smart eyeglasses, and/or the like), or a similar type of device or machine.

In some implementations, user device 250 may be a device of a doctor and may receive, from image processing platform 230, data that identifies a test result and/or a recommendation associated with the test result. In some implementations, user device 250 may be a device associated with a patient and may receive data that identifies the test result from image processing platform 230. In some implementations, user device 250 may be a device associated with a pharmacy and may receive, from image processing platform 230, a request for medication that may assist with one or more symptoms of a disease, with curing the disease, and/or the like. In some implementations, user device 250 may receive, from image processing platform 230, a set of instructions to perform one or more actions described elsewhere herein.

Network 260 includes one or more wired and/or wireless networks. For example, network 260 may include a cellular network (e.g., a fifth generation (5G) network, a fourth generation (4G) network, such as a long-term evolution (LTE) network, a third generation (3G) network, a code division multiple access (CDMA) network, a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as one or more examples. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
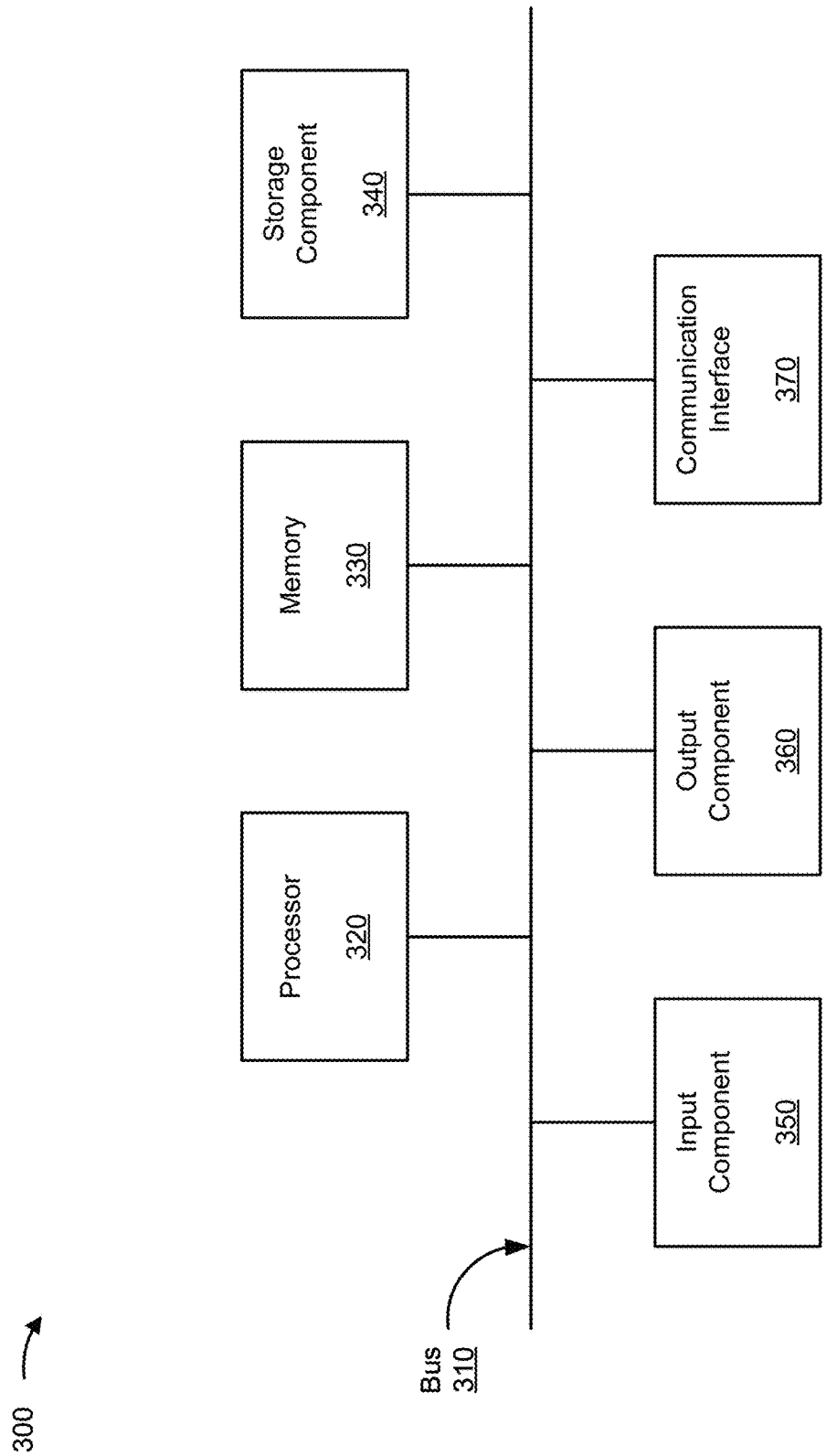
FIG. 3 is a diagram of example components of one or more devices of FIG. 2.

FIG. 3 is a diagram of example components of a device 300. Device 300 may correspond to imaging system 210, data storage device 220, image processing platform 230, computing resource 235, and/or user device 250. In some implementations, imaging system 210, data storage device 220, image processing platform 230, computing resource 235, and/or user device 250 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among multiple components of device 300. Processor 320 is implemented in hardware, firmware, and/or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a component for determining location (e.g., a global positioning system (GPS) component) and/or a sensor (e.g., an accelerometer, a gyroscope, an actuator, another type of positional or environmental sensor, and/or the like). Output component 360 includes a component that provides output information from device 300 (via, e.g., a display, a speaker, a haptic feedback component, an audio or visual indicator, and/or the like).

Communication interface 370 includes a transceiver-like component (e.g., a transceiver, a separate receiver, a separate transmitter, and/or the like) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. As used herein, the term "computer-readable medium" refers to a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
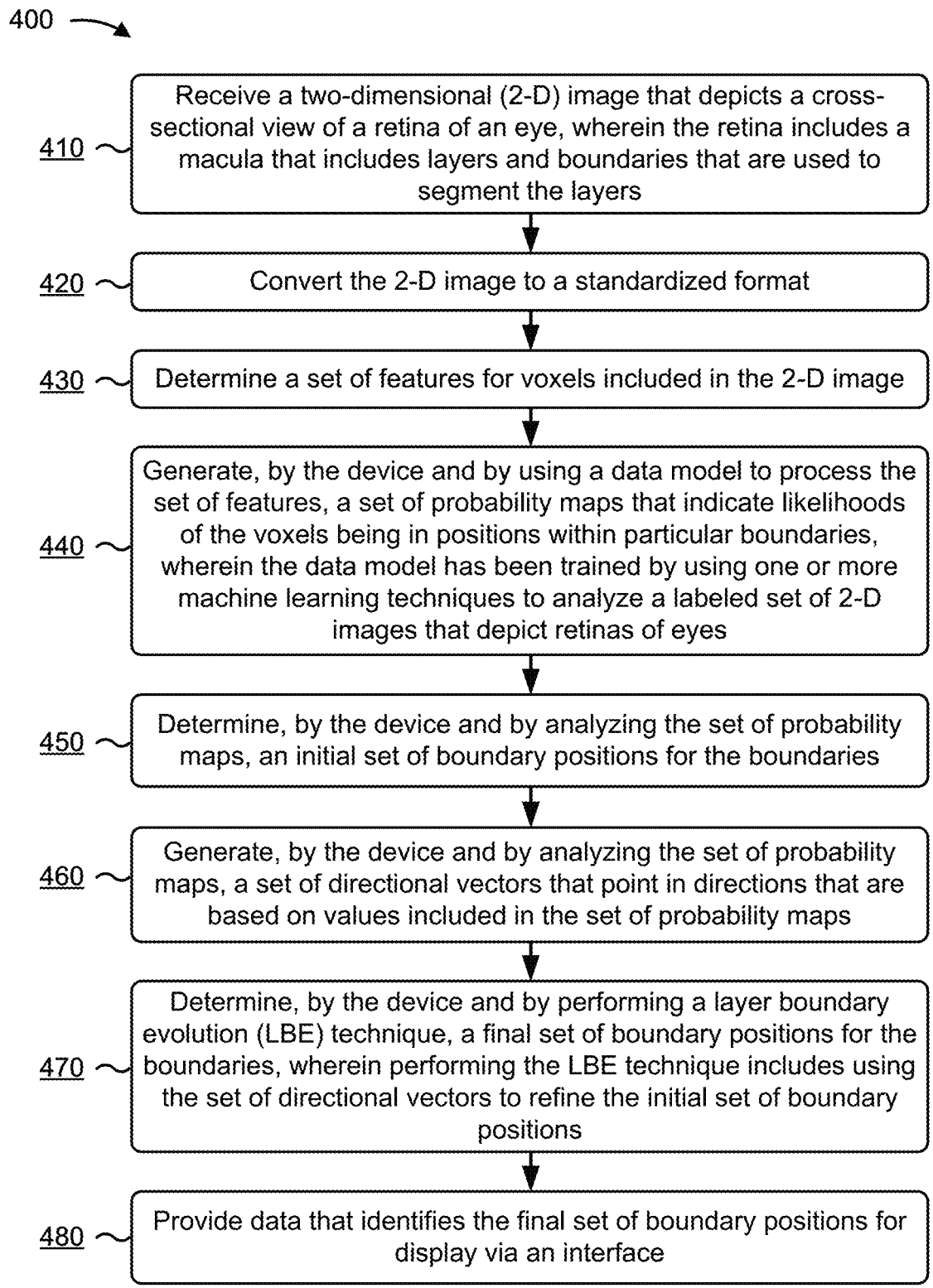
FIG. 4-6 are flowcharts of example processes for performing layer boundary evolution (LBE) on an image that depicts a cross-sectional view of a macula of an eye to determine boundary positions used to segment layers of the macula.

FIG. 4 is a flow chart of an example process 400 for performing layer boundary evolution (LBE) on an image that depicts a cross-sectional view of a macula of an eye to determine boundary positions used to segment layers of the macula. In some implementations, one or more process blocks of FIG. 4 may be performed by an image processing platform (e.g., image processing platform 230). In some implementations, one or more process blocks of FIG. 4 may be performed by another device or a group of devices separate from or including the image processing platform, such as imaging system 210, data storage device 220, computing resource 235, user device 250, and/or the like.

As shown in FIG. 4, process 400 may include receiving a two-dimensional (2-D) image that depicts a cross-sectional view of a retina of an eye, wherein the retina includes a macula that includes: layers, and boundaries that are used to segment the layers (block 410). For example, the image processing platform (e.g., using computing resource 235, processor 320, memory 330, storage component 340, input component 350, communication interface 370, and/or the like) may receive a 2-D image that depicts a cross-sectional view of a retina of an eye, as described above. In some implementations, the retina may include a macula that includes layers and boundaries that are used to segment the layers.

As further shown in FIG. 4, process 400 may include converting the 2-D image to a standardized format (block 420). For example, the image processing platform (e.g., using computing resource 235, processor 320, memory 330, storage component 340, and/or the like) may convert the 2-D image to a standardized format, as described above.

As further shown in FIG. 4, process 400 may include determining a set of features for voxels included in the 2-D image (block 430). For example, the image processing platform (e.g., using computing resource 235, processor 320, memory 330, storage component 340, and/or the like) may determine a set of features for voxels included in the 2-D image, as described above.

As further shown in FIG. 4, process 400 may include generating, by using a data model to process the set of features, a set of probability maps that indicate likelihoods of the voxels being in positions within particular boundaries, wherein the data model has been trained by using one or more machine learning techniques to analyze a labeled set of 2-D images that depict retinas of eyes (block 440). For example, the image processing platform (e.g., using computing resource 235, processor 320, memory 330, storage component 340, and/or the like) may generate, by using a data model to process the set of features, a set of probability maps that indicate likelihoods of the voxels being in positions within particular boundaries, as described above. In some implementations, the data model has been trained by using one or more machine learning techniques to analyze a labeled set of 2-D images that depict retinas of eyes.

As further shown in FIG. 4, process 400 may include determining, by analyzing the set of probability maps, an initial set of boundary positions for the boundaries (block 450). For example, the image processing platform (e.g., using computing resource 235, processor 320, memory 330, storage component 340, and/or the like) may determine, by analyzing the set of probability maps, an initial set of boundary positions for the boundaries, as described above.

As further shown in FIG. 4, process 400 may include generating, by analyzing the set of probability maps, a set of directional vectors that point in directions that are based on values included in the set of probability maps (block 460). For example, the image processing platform (e.g., using computing resource 235, processor 320, memory 330, storage component 340, and/or the like) may generate, by analyzing the set of probability maps, a set of directional vectors that point in directions that are based on values included in the set of probability maps, as described above.

As further shown in FIG. 4, process 400 may include determining, by performing a layer boundary evolution (LBE) technique, a final set of boundary positions for the boundaries, wherein performing the LBE technique includes using the set of directional vectors to refine the initial set of boundary positions (block 470). For example, the image processing platform (e.g., using computing resource 235, processor 320, memory 330, storage component 340, and/or the like) may determine, by performing an LBE technique, a final set of boundary positions for the boundaries, as described above. In some implementations, performing the LBE technique may include using the set of directional vectors to refine the initial set of boundary positions.

As further shown in FIG. 4, process 400 may include providing data that identifies the final set of boundary positions for display via an interface (block 480). For example, the image processing platform (e.g., using computing resource 235, processor 320, memory 330, storage component 340, output component 360, communication interface 370, and/or the like) may provide data that identifies the final set of boundary positions for display via an interface, as described above.

Process 400 may include additional implementations, such as any single implementation or any combination of implementations described below and/or in connection with one or more other processes described elsewhere herein.

In some implementations, the image processing platform may determine, after determining the final set of boundary positions, thickness levels of the layers of the macula based on the final set of boundary positions, and may determine whether the thickness levels of the layers are indicative of a disease, where providing the data that identifies the final set of boundary positions for display via the interface comprises providing, for display via the interface, an indication of whether the thickness levels of the layers are indicative of a presence or a severity of the disease.

In some implementations, the final set of boundary positions may be determined at a sub-voxel level. In some implementations, when determining the initial set of boundary positions, the image processing platform may use a Gaussian smoothing technique that determines a smoothness value for a corresponding boundary without determining a curvature value. In some implementations, the set of directional vectors may be generated using a vector field convolution (VFC) technique.

In some implementations, when determining the final set of boundary positions by performing the LBE technique, the image processing platform may reference a set of rules to determine, based on the set of directional vectors, a manner in which to refine the initial set of boundary positions.

In some implementations, the set of rules may comprise: a first rule indicating that a specific boundary position is to be added to the final set of boundary positions if two vertically-aligned directional vectors are pointed toward each other in opposite directions, a second rule indicating that the specific boundary position is not to be added to the final set of boundary positions if the two vertically-aligned directional vectors are pointed in a uniform direction, where the uniform direction is used to identify a next boundary position that is to be considered for the final set of boundary positions, or a third rule indicating that a smoothing technique is to be used when considering the specific boundary position if the two vertically-aligned directional vectors are pointed away from each other in opposite directions.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
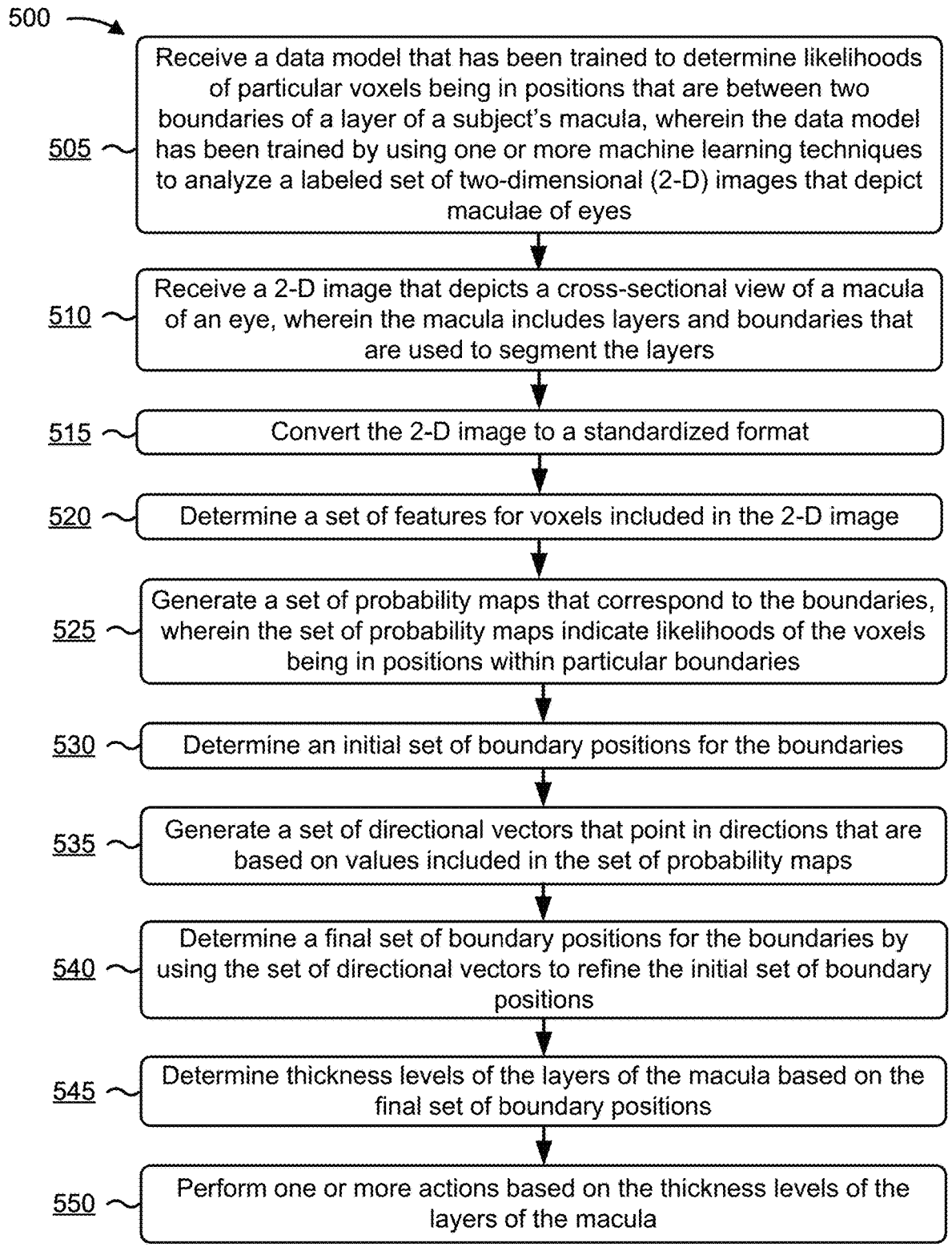

FIG. 5 is a flow chart of an example process 500 for performing LBE on an image that depicts a cross-sectional view of a macula of an eye to determine boundary positions used to segment layers of the macula. In some implementations, one or more process blocks of FIG. 5 may be performed by an image processing platform (e.g., image processing platform 230). In some implementations, one or more process blocks of FIG. 5 may be performed by another device or a group of devices separate from or including the image processing platform, such as imaging system 210, data storage device 220, computing resource 235, user device 250, and/or the like.

As shown in FIG. 5, process 500 may include receiving a data model that has been trained to determine likelihoods of particular voxels being in positions that are within particular boundaries of a layer of a subject's macula, wherein the data model has been trained by using one or more machine learning techniques to analyze a labeled set of 2-D images that depict maculae of eyes (block 505). For example, the image processing platform (e.g., using computing resource 235, processor 320, memory 330, storage component 340, input component 350, communication interface 370, and/or the like) may receive a data model that has been trained to determine likelihoods of particular voxels being in positions that are within particular boundaries of a layer of a subject's macula, as described above. In some implementations, the data model has been trained by using one or more machine learning techniques to analyze a labeled set of 2-D images that depict maculae of eyes.

As further shown in FIG. 5, process 500 may include receiving a 2-D image that depicts a cross-sectional view of a macula of an eye, wherein the macula includes: layers, and boundaries that are used to segment the layers (block 510). For example, the image processing platform (e.g., using computing resource 235, processor 320, memory 330, storage component 340, input component 350, communication interface 370, and/or the like) may receive a 2-D image that depicts a cross-sectional view of a macula of an eye, as described above. In some implementations, the macula may include layers, and boundaries that are used to segment the layers.

As further shown in FIG. 5, process 500 may include converting the 2-D image to a standardized format (block 515). For example, the image processing platform (e.g., using computing resource 235, processor 320, memory 330, storage component 340, and/or the like) may convert the 2-D image to a standardized format, as described above.

As further shown in FIG. 5, process 500 may include determining a set of features for voxels included in the 2-D image (block 520). For example, the image processing platform (e.g., using computing resource 235, processor 320, memory 330, storage component 340, and/or the like) may determine a set of features for voxels included in the 2-D image, as described above.

As further shown in FIG. 5, process 500 may include generating, by using the data model to process the set of features, a set of probability maps that correspond to the boundaries, wherein the set of probability maps indicate likelihoods of the voxels being in positions within particular boundaries (block 525). For example, the image processing platform (e.g., using computing resource 235, processor 320, memory 330, storage component 340, and/or the like) may generate, by using the data model to process the set of features, a set of probability maps that correspond to the boundaries, as described above. In some implementations, the set of probability maps may indicate likelihoods of the voxels being in positions within particular boundaries.

As further shown in FIG. 5, process 500 may include determining, by analyzing the set of probability maps, an initial set of boundary positions for the boundaries (block 530). For example, the image processing platform (e.g., using computing resource 235, processor 320, memory 330, storage component 340, and/or the like) may determine, by analyzing the set of probability maps, an initial set of boundary positions for the boundaries, as described above.

As further shown in FIG. 5, process 500 may include generating, by analyzing the set of probability maps, a set of directional vectors that point in directions that are based on values included in the set of probability maps (block 535). For example, the image processing platform (e.g., using computing resource 235, processor 320, memory 330, storage component 340, and/or the like) may generate, by analyzing the set of probability maps, a set of directional vectors that point in directions that are based on values included in the set of probability maps, as described above.

As further shown in FIG. 5, process 500 may include determining a final set of boundary positions for the boundaries by using the set of directional vectors to refine the initial set of boundary positions (block 540). For example, the image processing platform (e.g., using computing resource 235, processor 320, memory 330, storage component 340, and/or the like) may determine a final set of boundary positions for the boundaries by using the set of directional vectors to refine the initial set of boundary positions, as described above.

As further shown in FIG. 5, process 500 may include determining, after determining the final set of boundary positions, thickness levels of the layers of the macula based on the final set of boundary positions (block 545). For example, the image processing platform (e.g., using computing resource 235, processor 320, memory 330, storage component 340, and/or the like) may determine, after determining the final set of boundary positions, thickness levels of the layers of the macula based on the final set of boundary positions, as described above.

As further shown in FIG. 5, process 500 may include performing one or more actions based on the thickness levels of the layers of the macula (block 550). For example, the image processing platform (e.g., using computing resource 235, processor 320, memory 330, storage component 340, input component 350, output component 360, communication interface 370, and/or the like) may perform one or more actions based on the thickness levels of the layers of the macula, as described above.

Process 500 may include additional implementations, such as any single implementation or any combination of implementations described below and/or in connection with one or more other processes described elsewhere herein.

In some implementations, the device may be a first device, and the one or more actions may include one or more of: a first set of one or more actions to cause a result of whether the thickness levels of the layers are indicative of a severity of a disease to be displayed on an interface of a second device associated with a medical professional, a second set of one or more actions to cause medical equipment to perform a procedure on a patient, a third set of one or more actions to cause a prescription to be ordered for the patient, or a fourth set of one or more actions to cause a third device associated with the patient to be provided with a report that indicates the result of whether the thickness levels of the layers are indicative of the severity of the disease.

In some implementations, the final set of boundary positions may be determined at a sub-voxel level. In some implementations, the initial set of boundary positions may be determined using a shortest path technique. In some implementations, the set of directional vectors may be generated using a vector field convolution (VFC) technique.

In some implementations, when determining the final set of boundary positions by performing the LBE technique, the image processing platform may reference a set of rules to determine, based on the set of directional vectors, a manner in which to refine the initial set of boundary positions.

In some implementations, the set of rules may comprise: a first rule indicating that a specific boundary position is to be added to the final set of boundary positions if two vertically-aligned directional vectors are pointed toward each other in opposite directions, a second rule indicating that the specific boundary position is not to be added to the final set of boundary positions if the two vertically-aligned directional vectors are pointed in a uniform direction, where the uniform direction is used to identify a next boundary position that is to be considered for the final set of boundary positions, or a third rule indicating that a smoothing technique is to be used when considering the specific boundary position if the two vertically-aligned directional vectors are pointed away from each other in opposite directions.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
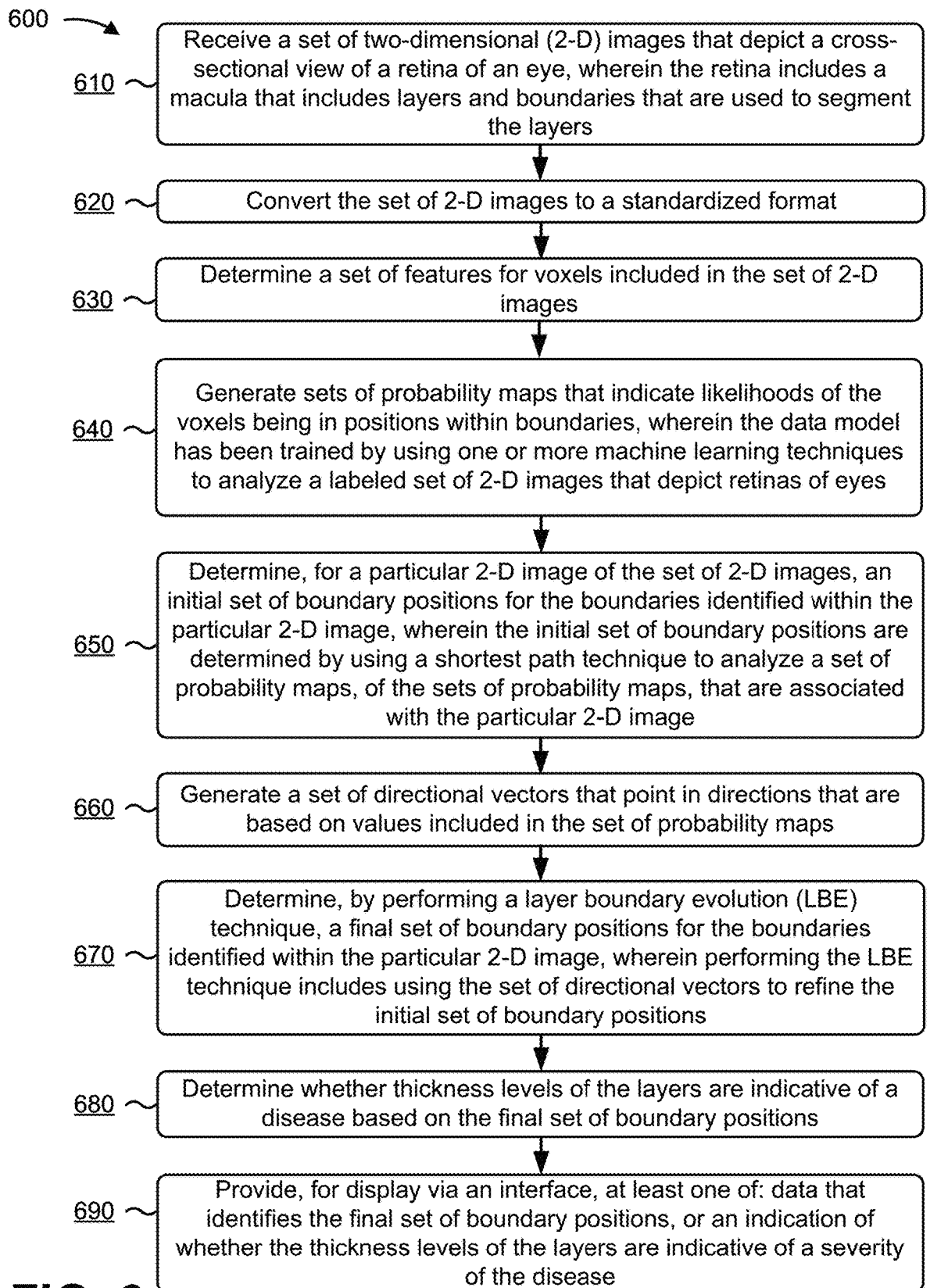

FIG. 6 is a flow chart of an example process 600 for performing layer boundary evolution (LBE) on an image that depicts a cross-sectional view of a macula of an eye to determine boundary positions used to segment layers of the macula. In some implementations, one or more process blocks of FIG. 6 may be performed by an image processing platform (e.g., image processing platform 230). In some implementations, one or more process blocks of FIG. 6 may be performed by another device or a group of devices separate from or including the image processing platform, such as imaging system 210, data storage device 220, computing resource 235, user device 250, and/or the like.

As shown in FIG. 6, process 600 may include receiving a set of 2-D images that depict a cross-sectional view of a retina of an eye, wherein the retina includes a macula that includes: layers, and boundaries that are used to segment the layers (block 610). For example, the image processing platform (e.g., using computing resource 235, processor 320, memory 330, storage component 340, input component 350, communication interface 370, and/or the like) may receive a set of 2-D images that depict a cross-sectional view of a retina of an eye, as described above. In some implementations, the retina may include a macula that includes layers, and boundaries that are used to segment the layers.

As further shown in FIG. 6, process 600 may include converting the set of 2-D images to a standardized format (block 620). For example, the image processing platform (e.g., using computing resource 235, processor 320, memory 330, storage component 340, and/or the like) may convert the set of 2-D images to a standardized format, as described above.

As further shown in FIG. 6, process 600 may include determining a set of features for voxels included in the set of 2-D images (block 630). For example, the image processing platform (e.g., using computing resource 235, processor 320, memory 330, storage component 340, and/or the like) may determine a set of features for voxels included in the set of 2-D images, as described above.

As further shown in FIG. 6, process 600 may include generating, by using a data model to process the set of features, sets of probability maps that indicate likelihoods of the voxels being in positions within particular boundaries, wherein the data model has been trained by using one or more machine learning techniques to analyze a labeled set of 2-D images that depict retinas of eyes (block 640). For example, the image processing platform (e.g., using computing resource 235, processor 320, memory 330, storage component 340, and/or the like) may generate, by using a data model to process the set of features, sets of probability maps that indicate likelihoods of the voxels being in positions within particular boundaries, as described above. In some implementations, the data model has been trained by using one or more machine learning techniques to analyze a labeled set of 2-D images that depict retinas of eyes.

As further shown in FIG. 6, process 600 may include determining, for a particular 2-D image of the set of 2-D images, an initial set of boundary positions for the boundaries identified within the particular 2-D image, wherein the initial set of boundary positions are determined by using a shortest path technique to analyze a set of probability maps, of the sets of probability maps, that are associated with the particular 2-D image (block 650). For example, the image processing platform (e.g., using computing resource 235, processor 320, memory 330, storage component 340, and/or the like) may determine, for a particular 2-D image of the set of 2-D images, an initial set of boundary positions for the boundaries identified within the particular 2-D image, as described above. In some implementations, the initial set of boundary positions may be determined by using a shortest path technique to analyze a set of probability maps, of the sets of probability maps, that are associated with the particular 2-D image.

As further shown in FIG. 6, process 600 may include generating, by analyzing the set of probability maps, a set of directional vectors that point in directions that are based on values included in the set of probability maps (block 660). For example, the image processing platform (e.g., using computing resource 235, processor 320, memory 330, storage component 340, and/or the like) may generate, by analyzing the set of probability maps, a set of directional vectors that point in directions that are based on values included in the set of probability maps, as described above.

As further shown in FIG. 6, process 600 may include determining, by performing a layer boundary evolution (LBE) technique, a final set of boundary positions for the boundaries identified within the particular 2-D image, wherein performing the LBE technique includes using the set of directional vectors to refine the initial set of boundary positions (block 670). For example, the image processing platform (e.g., using computing resource 235, processor 320, memory 330, storage component 340, and/or the like) may determine, by performing a layer boundary evolution (LBE) technique, a final set of boundary positions for the boundaries identified within the particular 2-D image, as described above. In some implementations, performing the LBE technique may include using the set of directional vectors to refine the initial set of boundary positions.

As further shown in FIG. 6, process 600 may include determining whether thickness levels of the layers are indicative of a disease based on the final set of boundary positions (block 680). For example, the image processing platform (e.g., using computing resource 235, processor 320, memory 330, storage component 340, and/or the like) may determine whether thickness levels of the layers are indicative of a disease based on the final set of boundary positions, as described above.

As further shown in FIG. 6, process 600 may include providing, for display via an interface, at least one of: data that identifies the final set of boundary positions, or an indication of whether the thickness levels of the layers are indicative of a severity of the disease (block 690). For example, the image processing platform (e.g., using computing resource 235, processor 320, memory 330, storage component 340, output component 360, communication interface 370, and/or the like) may provide, for display via an interface, at least one of: data that identifies the final set of boundary positions, or an indication of whether the thickness levels of the layers are indicative of a severity of the disease, as described above.

Process 600 may include additional implementations, such as any single implementation or any combination of implementations described below and/or in connection with one or more other processes described elsewhere herein.

In some implementations, the final set of boundary positions may be determined at a sub-voxel level. In some implementations, when converting the set of 2-D images to the standardized format, the image processing platform may flatten the particular 2-D image using a Gaussian smoothing technique, and may normalize intensity values associated with voxels in the particular 2-D image. In some implementations, the set of directional vectors may be generated using a vector field convolution (VFC) technique.

In some implementations, when determining the final set of boundary positions by performing the LBE technique, the image processing platform may reference a set of rules to determine, based on the set of directional vectors, a manner in which to refine the initial set of boundary positions.

In some implementations, the set of rules may include at least one of: a first rule indicating that a specific boundary position is to be added to the final set of boundary positions if two vertically-aligned directional vectors are pointed toward each other in opposite directions, a second rule indicating that the specific boundary position is not to be added to the final set of boundary positions if the two vertically-aligned directional vectors are pointed in a uniform direction, wherein the uniform direction is used to identify a next boundary position that is to be considered for the final set of boundary positions, or a third rule indicating that a smoothing technique is to be used when considering the specific boundary position if the two vertically-aligned directional vectors are pointed away from each other in opposite directions.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

Certain user interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
   receiving, by a device, a two-dimensional (2-D) image that depicts a cross-sectional view of a retina of an eye,
      wherein the retina includes a macula that includes:
         layers, and
         boundaries that are used to segment the layers;
   converting, by the device, the 2-D image to a standardized format;
   determining, by the device, a set of features for voxels included in the 2-D image;
   generating, by the device and by using a data model to process the set of features, a set of probability maps that indicate likelihoods of the voxels being in positions within particular boundaries,
      wherein the data model has been trained by using one or more machine learning techniques to analyze a labeled set of 2-D images that depict retinas of eyes;
   determining, by the device and by analyzing the set of probability maps, an initial set of boundary positions for the boundaries;
   generating, by the device and by analyzing the set of probability maps, a set of directional vectors that point in directions that are based on values included in the set of probability maps;
   determining, by the device and by performing a layer boundary evolution (LBE) technique, a final set of boundary positions for the boundaries,
      wherein performing the LBE technique includes using the set of directional vectors to refine the initial set of boundary positions,
      wherein determining the final set of boundary positions comprises referencing a set of rules to determine, based on the set of directional vectors, a manner in which to refine the initial set of boundary positions, and
      wherein the set of rules comprises:
         a first rule indicating that a specific boundary position is to be added to the final set of boundary positions if two vertically-aligned directional vectors are pointed toward each other in opposite directions,
         a second rule indicating that the specific boundary position is not to be added to the final set of boundary positions if the two vertically-aligned directional vectors are pointed in a uniform direction, wherein the uniform direction is used to identify a next boundary position that is to be considered for the final set of boundary positions, or a third rule indicating that a smoothing technique is to be used when considering the specific boundary position if the two vertically-aligned directional vectors are pointed away from each other in opposite directions; and providing, by the device, data that identifies the final set of boundary positions for display via an interface.

2. The method of claim 1, further comprising:

determining, after determining the final set of boundary positions, thickness levels of the layers of the macula based on the final set of boundary positions; and determining whether the thickness levels of the layers are indicative of a disease; and wherein providing the data that identifies the final set of boundary positions for display via the interface comprises:

providing, for display via the interface, an indication of whether the thickness levels of the layers indicate a existence or a severity of the disease.

3. The method of claim 1, wherein the final set of boundary positions are determined at a sub-voxel level.

4. The method of claim 1, wherein determining the initial set of boundary positions comprises:

using a Gaussian smoothing technique that determines a smoothness value for a corresponding boundary without determining a curvature value.

5. The method of claim 1, wherein the set of directional vectors are generated using a vector field convolution (VFC) technique.

6. The method of claim 1, wherein the 2-D image is associated with a B-scan.

7. The method of claim 6, wherein determining the initial set of boundary positions comprise of determining derivatives for a set of amplitude scans within the B-scan.

8. A device, comprising:

one or more memories; and one or more processors, operatively coupled to the one or more memories, configured to:

receive a data model that has been trained to determine likelihoods of particular voxels being in positions that are within specific boundaries of a layer of a subject's macula, wherein the data model has been trained by using one or more machine learning techniques to analyze a labeled set of two-dimensional (2-D) images that depict maculae of eyes;

receive a 2-D image that depicts a cross-sectional view of a macula of an eye, wherein the macula includes:

layers, and boundaries that are used to segment the layers;

convert the 2-D image to a standardized format;

determine a set of features for voxels included in the 2-D image;

generate, by using the data model to process the set of features, a set of probability maps that correspond to the boundaries, wherein the set of probability maps indicate likelihoods of the voxels being in positions within particular boundaries;

determine, by analyzing the set of probability maps, an initial set of boundary positions for the boundaries;

generate, by analyzing the set of probability maps, a set of directional vectors that point in directions that are based on values included in the set of probability maps;

determine, performing a layer boundary evolution (LBE) technique, a final set of boundary positions for the boundaries by using the set of directional vectors to refine the initial set of boundary positions, wherein determining the set of boundary positions comprises referencing a set of rules to determine, based on the set of directional vectors, a manner in which to refine the initial set of boundary positions, and wherein the set of rules comprises:

a first rule indicating that a specific boundary position is to be added to the final set of boundary positions if two vertically-aligned directional vectors are pointed toward each other in opposite directions, a second rule indicating that the specific boundary position is not to be added to the final set of boundary positions if the two vertically-aligned directional vectors are pointed in a uniform direction, wherein the uniform direction is used to identify a next boundary position that is to be considered for the final set of boundary positions, or a third rule indicating that a smoothing technique is to be used when considering the specific boundary position if the two vertically-aligned directional vectors are pointed away from each other in opposite directions;

determine, after determining the final set of boundary positions, thickness levels of the layers of the macula based on the final set of boundary positions; and perform one or more actions based on the thickness levels of the layers of the macula.

9. The device of claim 8, wherein the device is a first device;

wherein the one or more actions include one or more of:

a first set of one or more actions to cause a result of whether the thickness levels of the layers are indicative of a severity of a disease to be displayed on an interface of a second device associated with a medical professional, a second set of one or more actions to cause medical equipment to perform a procedure on a patient, a third set of one or more actions to cause a prescription to be ordered for the patient, or a fourth set of one or more actions to cause a third device associated with the patient to be provided with a report that indicates the result of whether the thickness levels of the layers are indicative of the severity of the disease.

10. The device of claim 8, wherein the final set of boundary positions are determined at a sub-voxel level.

11. The device of claim 8, wherein the initial set of boundary positions are determined using a shortest path technique.

12. The device of claim 8, wherein the set of directional vectors are generated using a vector field convolution (VFC) technique.

13. The device of claim 8, wherein the 2-D image is associated with a B-scan.

14. The device of claim 13, wherein determining the initial set of boundary positions comprise of determining derivatives for a set of amplitude scans within the B-scan.

15. A non-transitory computer-readable medium storing instructions, the instructions comprising:
one or more instructions that, when executed by one or more processors of a device, cause the one or more processors to:
receive a set of two-dimensional (2-D) images that depict a cross-sectional view of a retina of an eye, wherein the retina includes a macula that includes:
layers, and
boundaries that are used to segment the layers;
convert the set of 2-D images to a standardized format;
determine a set of features for voxels included in the set of 2-D images;
generate, by using a data model to process the set of features, sets of probability maps that indicate likelihoods of the voxels being in positions within particular boundaries,
wherein the data model has been trained by using one or more machine learning techniques to analyze a labeled set of 2-D images that depict retinas of eyes;
determine, for a particular 2-D image of the set of 2-D images, an initial set of boundary positions for the boundaries identified within the particular 2-D image,
wherein the initial set of boundary positions are determined by using a shortest path technique to analyze a set of probability maps, of the sets of probability maps, that are associated with the particular 2-D image;
generate, by analyzing the set of probability maps, a set of directional vectors that point in directions that are based on values included in the set of probability maps;
determine, by performing a layer boundary evolution (LBE) technique, a final set of boundary positions for the boundaries identified within the particular 2-D image,
wherein performing the LBE technique includes using the set of directional vectors to refine the initial set of boundary positions,
wherein determining the final set of boundary positions comprises referencing a set of rules to determine, based on the set of directional vectors, a manner in which to refine the initial set of boundary positions, and
wherein the set of rules comprises:
a first rule indicating that a specific boundary position is to be added to the final set of boundary positions if two vertically-aligned directional vectors are pointed toward each other in opposite directions,
a second rule indicating that the specific boundary position is not to be added to the final set of boundary positions if the two vertically-aligned directional vectors are pointed in a uniform direction,
wherein the uniform direction is used to identify a next boundary position that is to be considered for the final set of boundary positions, or
a third rule indicating that a smoothing technique is to be used when considering the specific boundary position if the two vertically-aligned directional vectors are pointed away from each other in opposite directions;
determine whether thickness levels of the layers are indicative of a disease based on the final set of boundary positions; and
provide, for display via an interface, at least one of:
data that identifies the final set of boundary positions, or
an indication of whether the thickness levels of the layers are indicative of a severity of the disease.

16. The non-transitory computer-readable medium of claim 15, wherein the final set of boundary positions are determined at a sub-voxel level.

17. The non-transitory computer-readable medium of claim 15, wherein the one or more instructions, that cause the one or more processors to convert the set of 2-D images to the standardized format, cause the one or more processors to:
flatten the particular 2-D image using a Gaussian smoothing technique, and
normalize intensity values associated with voxels in the particular 2-D image.

18. The non-transitory computer-readable medium of claim 15, wherein the set of directional vectors are generated using a vector field convolution (VFC) technique.

19. The non-transitory computer-readable medium of claim 15, wherein the 2-D image is associated with a B-scan.

20. The non-transitory computer-readable medium of claim 19, wherein determining the initial set of boundary positions comprise of determining derivatives for a set of amplitude scans within the B-scan.

* * * * *